(12) United States Patent
Takemura et al.

(10) Patent No.: US 6,586,604 B2
(45) Date of Patent: Jul. 1, 2003

(54) TRICYCLIC AMINE DERIVATIVES

(75) Inventors: Makoto Takemura, Tokyo (JP);
Hisashi Takahashi, Tokyo (JP);
Kenichi Kimura, Tokyo (JP); Rie Miyauchi, Tokyo (JP); Hitoshi Ohki, Tokyo (JP); Katsuhiro Kawakami, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/875,852

(22) Filed: Jun. 8, 2001

(65) Prior Publication Data

US 2001/0037030 A1 Nov. 1, 2001

Related U.S. Application Data

(62) Division of application No. 09/284,871, filed on Apr. 22, 1999.

(30) Foreign Application Priority Data

Oct. 25, 1996 (JP) .............................................. 8-283446
Apr. 10, 1997 (JP) .............................................. 9-091254

(51) Int. Cl.$^7$ ............................................ C07D 401/04
(52) U.S. Cl. ...................... 548/439; 546/156; 514/312; 514/456; 514/470; 548/429; 548/430
(58) Field of Search ........................................ 548/439

(56) References Cited

FOREIGN PATENT DOCUMENTS

| JP | 64-56673 | 3/1989 |
| JP | 6-239867 | 8/1994 |
| JP | 6-247962 | 9/1994 |
| JP | 7-149758 | 6/1995 |
| JP | 8-48629 | 2/1996 |

OTHER PUBLICATIONS

Filigheddu et al, *Tetrehedron Letters,* 40:6503–6505 (1999).
Huh et al, *Tetrahedron,* 51:5935–5950 (1999).

*Primary Examiner*—Venkataraman Balasubramanian
(74) *Attorney, Agent, or Firm*—Sughrue Mion, PLLC

(57) ABSTRACT

The present invention relates to a compound having a tricyclic amine substituent which may have various substituents, the compound being represented by formula (I), a salt or hydrate thereof, and a hydrate of the salt and a drug containing them as an active ingredient. They exhibit excellent antimicrobial activity against Gram negative bacteria and Gram positive bacteria with a satisfactory fate and safety and are useful in the treatment of infectious diseases.

(I)

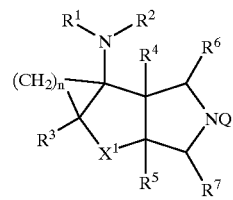

wherein Q preferably represents the following partial structure which may have various substituents:

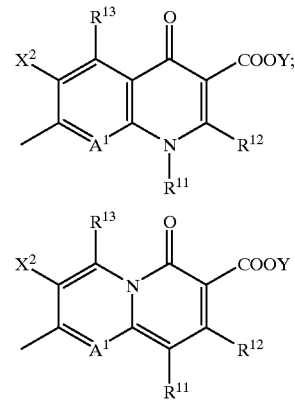

8 Claims, No Drawings

TRICYCLIC AMINE DERIVATIVES

CROSS-REFERENCE TO RELATED APPLICATION

This application is a Divisional of application Ser. No. 09/284,871, filed Apr. 22, 1999, the disclosure of which is incorporated herein by reference.

INDUSTRIAL FIELD

This invention relates to an antimicrobial compound useful as a drug for humans, animals or fishes or an antimicrobial preservative and an antimicrobial agent or preparation containing the same.

BACKGROUND ART

Since the discovery of Norfloxacin, synthetic quinolone antimicrobial agents have been improved in antimicrobial activity and pharmacokinetics, and many compounds have been launched for clinical use as a chemotherapeutic agent effective on all most all systemic infectious diseases.

However, bacteria having low sensitivity to the synthetic quinolone antimicrobial agents have recently been increasing in the clinical field. For example, bacteria which have not only resistance to drugs other than synthetic quinolone antimicrobial agents but low sensitivity to synthetic quinolone antimicrobial agents, as exemplified by *Staphylococcus aureaus* insensitive to β-lactam antibiotics (MRSA), have been increasing. Therefore, more effective drugs have been keenly demanded in the field of clinics.

Further, it has been revealed that synthetic quinolone antimicrobial agents tend to induce convulsion in a combined use with a non-steroid antiinflammatory agent or involve side effects such as phototoxicity. Therefore, development of safer synthetic quinolone antimicrobial agents has been sought.

DISCLOSURE OF THE INVENTION

In the light of these circumstances, the inventors have conducted extensive investigation for the purpose of providing excellent compounds fulfilling the above demands. As a result, they have found that tricyclic amine derivatives represented by formula (I) shown below and their salts and hydrates thereof have high antimicrobial activity broadly on Gram positive bacteria and Gram negative bacteria, exhibiting potent antimicrobial activity particularly on quinolone-resistant bacteria including MRSA, and also show satisfactory pharmacokinetics and safety.

The present invention relates to a compound represented by formula (I) shown below and its salt and their hydrates.

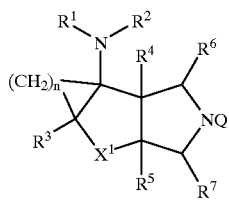

(I)

wherein $R^1$ and $R^2$ each independently represents a hydrogen atom or an alkyl group having 1 to 6 carbon atoms which may be substituted with one or more substituents selected from the group consisting of a hydroxyl group, a halogen atom, an alkylthio group having 1 to 6 carbon atoms, and an alkoxyl group having 1 to 6 carbon atoms;

$R^3$ represents a hydrogen atom, a hydroxyl group, a halogen atom, a carbamoyl group, an alkyl group having 1 to 6 carbon atoms, an alkoxyl group having 1 to 6 carbon atoms or an alkylthio group having 1 to 6 carbon atoms, in which the alkyl group may be substituted with one or more substituents selected from the group consisting of a hydroxyl group, a halogen atom, and an alkoxyl group having 1 to 6 carbon atoms;

$R^4$ and $R^5$ each independently represents a hydrogen atom, a halogen atom, an alkyl group having 1 to 6 carbon atoms or an alkoxyl group having 1 to 6 carbon atoms, in which the alkyl group may be substituted with one or more substituents selected from the group consisting of a hydroxyl group, a halogen atom, and an alkoxyl group having 1 to 6 carbon atoms;

$R^6$ and $R^7$ each independently represents a hydrogen atom or an alkyl group having 1 to 6 carbon atoms;

$X^1$ represents an oxygen atom, a sulfur atom, a partial structure:

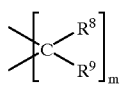

(wherein $R^8$ and $R^9$ each independently represents a hydrogen atom or an alkyl group having 1 to 6 carbon atoms; and m represents an integer 1 or 2) or a partial structure:

(wherein $R^{10}$ represents a hydrogen atom, a formyl group, an acyl group having 2 to 5 carbon atoms or an alkyl group having 1 to 6 carbon atoms);

n represents an integer 1 or 2; and

Q represents a partial structure represented by formula:

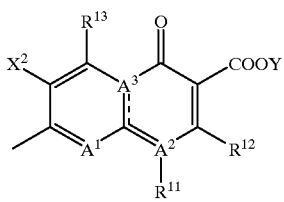

(wherein $R^{11}$ represents an alkyl group having 1 to 6 carbon atoms, an alkenyl group having 2 to 6 carbon atoms, a halogenoalkyl group having 1 to 6 carbon atoms, a substituted or unsubstituted cycloalkyl group having 3 to 6 carbon atoms, a substituted or unsubstituted aryl group, a substituted or unsubstituted heteroaryl group, an alkoxyl group having 1 to 6 carbon atoms, or an alkylamino group having 1 to 6 carbon atoms;

$R^{12}$ represents a hydrogen atom or an alkylthio group having 1 to 6 carbon atoms;

$R^{11}$ and $R^{12}$ may be taken together with part of the mother skeleton to which they are bonded to form a cyclic structure that may have a sulfur atom as a ring-constituting atom and an alkyl group having 1 to 6 carbon atoms as a substituent;

$R^{13}$ represents a hydrogen atom, an amino group, a hydroxyl group, a thiol group, a halogenomethyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, in which the amino group may have one or two substituents selected from the group consisting of a formyl group, an alkyl group having 1 to 6 carbon atoms, and an acyl group having 2 to 5 carbon atoms;

$X^2$ represents a halogen atom or a hydrogen atom;

$A^1$ represents a nitrogen atom or a partial structure represented by formula (II):

(II)

wherein $X^3$ represents a hydrogen atom, an amino group, a halogen atom, a cyano group, a halogenomethyl group, a halogenomethoxyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, in which the amino group may have one or two substituents selected from the group consisting of a formyl group, an alkyl group having 1 to 6 carbon atoms and an acyl group having 2 to 5 carbon atoms; and $X^3$ and $R^{11}$ may be taken together with part of the mother skeleton to which they are bonded to form a cyclic structure that may contain an oxygen atom, a nitrogen atom or a sulfur atom as a ring-constituting atom and an alkyl group having 1 to 6 carbon atoms as a substituent;

$A^2$ and $A^3$ each represents a nitrogen atom or a carbon atoms provided that $A^2$, $A^3$, and the carbon atom to which they are bonded form a partial structure:

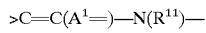

or a partial structure:

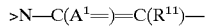

wherein > indicates the carbon atom or the nitrogen atom has two bonds (hereinafter the same); and Y represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms, or a phenylalkyl group composed of an alkylene group having 1 to 6 carbon atoms and a phenyl group).

The present invention also relates to:
(1) the compound of formula (I), wherein Q is a structure represented by formula:

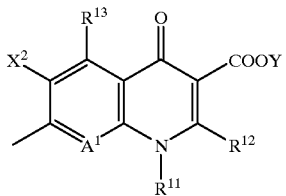

or a structure represented by formula:

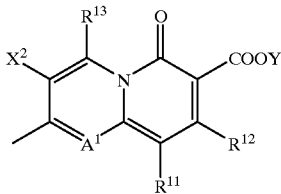

a salt or hydrate thereof, and a hydrate of the salt;
(2) the compound of formula (I), wherein Q is a structure represented by formula:

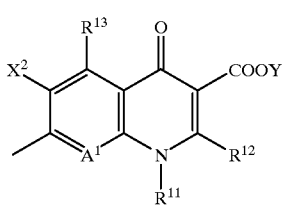

a salt or hydrate thereof, and a hydrate of the salt;
(3) the compound of formula (I), wherein Q is a 9-fluoro-2,3-dihydro-3-(S)-methyl-7-oxo-7H-pyrido [1,2,3-de][1,4]benzoxazin-6-carboxylic acid-10-yl group of formula:

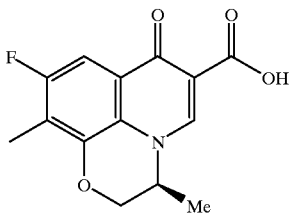

a salt or hydrate thereof, and a hydrate of the salt;
(4) the compound of formula (I), wherein Q is a 6-fluoro-1-[2-(S)-fluoro-1-(R)-cyclopropyl]-8-methoxy-1,4-dihydro-4-oxoquinolin-3-carboxylic acid-7-yl group of formula:

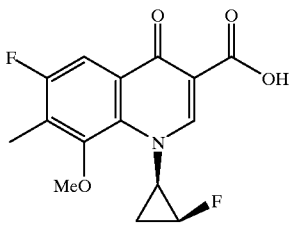

a salt or hydrate thereof, and a hydrate of the salt;
(5) the compound of formula (I), wherein Q is a 6-fluoro-1-[2-(S)-fluoro-1-(R)-cyclopropyl]-8-methyl-1,4- dihydro-4-oxoquinolin-3-carboxylic acid-7-yl group of formula:

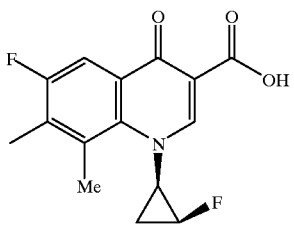

a salt or hydrate thereof, and a hydrate of the salt;
(6) the compound of formula (I), wherein Q is a 5-amino-6-fluoro-1-[2-(S)-fluoro-1-(R)-cyclopropyl]-8-methyl-1,4-dihydro-4-oxoquinolin-3-carboxylic acid-7-yl group of formula:

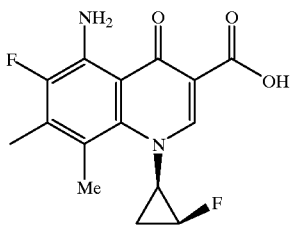

a salt or hydrate thereof, and a hydrate of the salt;
(7) the compound of formula (I), wherein $X^1$ is a partial structure represented by formula:

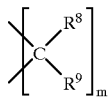

wherein $R^8$ and $R^9$ each independently represents a hydrogen atom or an alkyl group having 1 to 6 carbon atoms; and m represents an integer 1 or 2, a salt or a hydrate thereof, and a hydrate of the salt;
(8) the compound of formula (I), wherein $R^8$ and $R^9$ are each a hydrogen atom, and m is 1, a salt or hydrate thereof, and a hydrate of the salt;
(9) the compound of formula (I), wherein n is 1, a salt or hydrate thereof, and a hydrate of the salt;
(10) the compound of formula (I), wherein n is 1, and $X^1$ is a partial structure represented by formula:

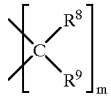

wherein $R^8$ and $R^9$ each independently represents a hydrogen atom or an alkyl group having 1 to 6 carbon atoms, and m represents an integer 1 or 2, a salt or hydrate thereof, and a hydrate of the salt;
(11) the above compound in which $R^8$ and $R^9$ are each a hydrogen atom, a salt or hydrate thereof, and a hydrate of the salt;
(12) the above compound in which m is 1, a salt or hydrate thereof, and a hydrate of the salt;
(13) the above compound in which $R^8$ and $R^9$ are each a hydrogen atom, and m is 1, a salt and hydrate thereof, and a hydrate of the salt;

(14) the compound of formula (I) which is a stereochemically pure compound, a salt or hydrate thereof, and a hydrate of the salt;
(15) the above compound in which $R^{11}$ is a cyclopropyl group having a halogen atom as a substituent, a salt or hydrate thereof, and a hydrate of the salt;
(16) the above compound in which the cyclopropyl group having a halogen atom as a substituent is a 1,2-cis-halogenocyclopropyl group, a salt or hydrate thereof, and a hydrate of the salt;
(17) the above compound in which the cyclopropyl group having a halogen atom as a substituent is a stereochemically pure substituent, a salt or hydrate thereof, and a hydrate of the salt;
(18) the above compound in which the cyclopropyl group having a halogen atom as a substituent is a (1R,2S)-2-halogenocyclopropyl group, a salt or hydrate thereof, and a hydrate of the salt;
(19) the above compound in which the halogen atom of the cyclopropyl group having a halogen atom as a substituent is a fluorine atom, a salt or hydrate thereof, and a hydrate of the salt;
(20) the above compound in which each of $R^3$, $R^4$, $R^5$, $R^6$, and $R^7$ is a hydrogen atom, a salt or hydrate thereof, and a hydrate of the salt;
(21) the above compound in which n is 1, a salt or hydrate thereof, and a hydrate of the salt;
(22) the compound of formula (I), wherein $X^1$ is a partial structure represented by formula:

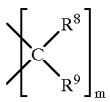

wherein $R^8$ and $R^9$ each independently represents a hydrogen atom or an alkyl group having 1 to 6 carbon atoms; and m is an integer 1 or 2, a salt or hydrate thereof, and a hydrate of the salt;
(23) the above compound in which $R^8$ and $R^9$ are each a hydrogen atom, a salt or hydrate thereof, and a hydrate of the salt;
(24) the above compound in which $R^8$ and $R^9$ are each a hydrogen atom; and m is 1, a salt or hydrate thereof, and a hydrate of the salt;
(25) the above compound in which $R^1$ and $R^2$ are each a hydrogen atom, a salt or hydrate thereof, and a hydrate of the salt;
(26) a drug characterized by containing the above-described compound, a salt or hydrate thereof, or a hydrate of the salt as an active ingredient;
(27) an antimicrobial agent characterized by containing the above-described compound, a salt or hydrate thereof, or a hydrate of the salt as an active ingredient;
(28) a treating agent for an infectious disease characterized by containing the above-described compound, a salt or hydrate thereof, or a hydrate of the salt as an active ingredient;
(29) a method for treating a disease characterized by administering the above-described compound, a salt or hydrate thereof or a hydrate of the salt;
(30) a method for treating an infectious disease characterized by administering the above-described compound, a salt or hydrate thereof or a hydrate of the salt;
(31) a method for producing a drug characterized by compounding the above-described compound, a salt or hydrate thereof or a hydrate of the salt as an active ingredient;

(32) a method for producing an antimicrobial agent characterized by compounding the above-described compound, a salt or hydrate thereof or a hydrate of the salt as an active ingredient;

(33) a method for producing a treating agent for an infectious disease characterized by compounding the above-described compound, a salt or hydrate thereof or a hydrate of the salt as an active ingredient;

(34) use of the above-described compound, a salt or hydrate thereof or a hydrate of the salt for production of a drug;

(35) use of the above-described compound, a salt or hydrate thereof or a hydrate of the salt for production of an antimicrobial agent;

(36) use of the above-described compound, a salt or hydrate thereof or a hydrate of the salt for production of a treating agent for an infectious disease;

(37) a compound represented by formula:

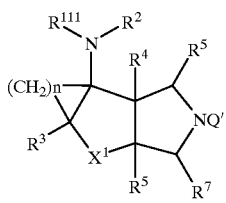

wherein $R^{111}$ represents a hydrogen atom, an alkyl group having 1 to 6 carbon atoms, or a protective group for amino group;

$R^2$ represents a hydrogen atom or an alkyl group having 1 to 6 carbon atoms;

in which the alkyl group as $R^{111}$ or $R^2$ may have one or more substituents selected from the group consisting of a hydroxyl group, a halogen atom, an alkylthio group having 1 to 6 carbon atoms, and an alkoxyl group having 1 to 6 carbon atoms;

$R^3$ represents a hydrogen atom, a hydroxyl group, a halogen atom, a carbamoyl group, an alkyl group having 1 to 6 carbon atoms, an alkoxyl group having 1 to 6 carbon atoms, or an alkylthio group having 1 to 6 carbon atoms, in which the alkyl group may have one or more substituents selected from the group consisting of a hydroxyl group, a halogen atom, and an alkoxyl group having 1 to 6 carbon atoms;

$R^4$ and $R^5$ each independently represents a hydrogen atom, a halogen atom, an alkyl group having 1 to 6 carbon atoms, or an alkoxyl group having 1 to 6 carbon atoms, in which the alkyl group may have one or more substituents selected from the group consisting of a hydroxyl group, a halogen atom, and an alkoxyl group having 1 to 6 carbon atoms;

$R^6$ and $R^7$ each independently represents a hydrogen atom or an alkyl group having 1 to 6 carbon atoms;

$X^1$ represents an oxygen atom, a sulfur atom, a partial structure:

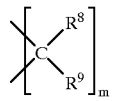

(wherein $R^8$ and $R^9$ each independently represents a hydrogen atom or an alkyl group having 1 to 6 carbon atoms; and m represents an integer 1 or 2) or a partial structure:

(wherein $R^{10}$ represents a hydrogen atom, a formyl group, an acyl group having 2 to 5 carbon atoms or an alkyl group having 1 to 6 carbon atoms);

n represents an integer 1 or 2; and

Q' represents a protective group for amino group, a salt or hydrate thereof, and a hydrate of the salt;

(38) the above compound in which the protective group for amino group is a protective group selected from the group consisting of a substituted or unsubstituted alkoxycarbonyl group, a substituted or unsubstituted aralkyloxycarbonyl group, a substituted or unsubstituted acyl group, a substituted or unsubstituted alkyl group, a substituted or unsubstituted aralkyl group, and a silyl group, a salt or hydrate thereof, and a hydrate of the salt;

(39) the above compound in which the protective group for amino group is a protective group selected from the group consisting of a t-butoxycarbonyl group, a 2,2,2-trichloroethoxycarbonyl group, a benzyloxycarbonyl group, a p-methoxybenzyloxycarbonyl group, a p-nitrobenzyloxycarbonyl group, an acetyl group, a methoxyacetyl group, a trifluoroacetyl group, a chloroacetyl group, a pivaloyl group, a formyl group, a benzoyl group, a t-butyl group, a benzyl group, a p-nitrobenzyl group, a p-methoxybenzyl group, a triphenylmethyl group, a methoxymethyl group, a t-butoxymethyl group, a tetrahydropyranyl group, a 2,2,2-trichloroethoxymethyl group, a trimethylsilyl group, an isopropyldimethylsilyl group, a t-butyldimethylsilyl group, a tribenzylsilyl group, and a t-butyldiphenylsilyl group, a salt or hydrate thereof, and a hydrate of the salt;

(40) the above compound in which $R^{111}$ and Q' are not the same protective groups, a salt or hydrate thereof, and a hydrate of the salt;

(41) the above compound in which n is 1, a salt or hydrate thereof, and a hydrate of the salt;

(42) the above compound in which each of $R^2$, $R^3$, $R^4$, $R^5$, $R^6$, and $R^7$ is a hydrogen atom, a salt or hydrate thereof, and a hydrate of the salt;

(43) the above compound in which $X^1$ is a partial structure of formula:

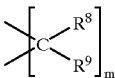

wherein $R^8$ and $R^9$ each independently represents a hydrogen atom or an alkyl group having 1 to 6 carbon atoms; and m represents an integer 1 or 2, a salt or hydrate thereof, and a hydrate of the salt;

(44) the above compound in which m is 1, a salt or hydrate thereof, and a hydrate of the salt;

(45) a compound represented by formula:

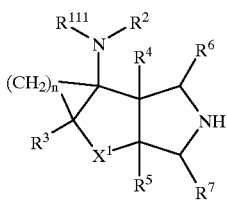
(VI)

wherein $R^{111}$ represents a hydrogen atom, an alkyl group having 1 to 6 carbon atoms, or a protective group for amino group;

$R^2$ represents a hydrogen atom or an alkyl group having 1 to 6 carbon atoms;

in which the alkyl group as $R^{111}$ or $R^2$ may have one or more substituents selected from the group consisting of a hydroxyl group, a halogen atom, an alkylthio group having 1 to 6 carbon atoms, and an alkoxyl group having 1 to 6 carbon atoms;

$R^3$ represents a hydrogen atom, a hydroxyl group, a halogen atom, a carbamoyl group, an alkyl group having 1 to 6 carbon atoms, an alkoxyl group having 1 to 6 carbon atoms, or an alkylthio group having 1 to 6 carbon atoms, in which the alkyl group may have one or more substituents selected from the group consisting of a hydroxyl group, a halogen atom, and an alkoxyl group having 1 to 6 carbon atoms;

$R^4$ and $R^5$ each independently represents a hydrogen atom, a halogen atom, an alkyl group having 1 to 6 carbon atoms, or an alkoxyl group having 1 to 6 carbon atoms, in which the alkyl group may have one or more substituents selected from the group consisting of a hydroxyl group, a halogen atom, and an alkoxyl group having 1 to 6 carbon atoms;

$R^6$ and $R^7$ each independently represents a hydrogen atom or an alkyl group having 1 to 6 carbon atoms;

$X^1$ represents an oxygen atom, a sulfur atom, a partial structure:

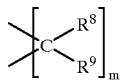

(wherein $R^8$ and $R^9$ each independently represents a hydrogen atom or an alkyl group having 1 to 6 carbon atoms; and m represents an integer 1 or 2) or a partial structure:

(wherein $R^{10}$ represents a hydrogen atom, a formyl group, an acyl group having 2 to 5 carbon atoms or an alkyl group having 1 to 6 carbon atoms); and n represents an integer 1 or 2, a salt or hydrate thereof, and a hydrate of the salt;

(46) the above compound in which the protective group for amino group is a protective group selected from the group consisting of a substituted or unsubstituted alkoxycarbonyl group, a substituted or unsubstituted aralkyloxycarbonyl group, a substituted or unsubstituted acyl group, a substituted or unsubstituted alkyl group, a substituted or unsubstituted aralkyl group, and a silyl group, a salt or hydrate thereof, and a hydrate of the salt;

(47) the above compound in which the protective group for amino group is a protective group selected from the group consisting of a t-butoxycarbonyl group, a 2,2,2-trichloroethoxycarbonyl group, a benzyloxycarbonyl group, a p-methoxybenzyloxycarbonyl group, a p-nitrobenzyloxycarbonyl group, an acetyl group, a methoxyacetyl group, a trifluoroacetyl group, a chloroacetyl group, a pivaloyl group, a formyl group, a benzoyl group, a t-butyl group, a benzyl group, a p-nitrobenzyl group, a p-methoxybenzyl group, a triphenylmethyl group, a methoxymethyl group, a t-butoxymethyl group, a tetrahydropyranyl group, a 2,2,2-trichloroethoxymethyl group, a trimethylsilyl group, an isopropyldimethylsilyl group, a t-butyldimethylsilyl group, a tribenzylsilyl group, and a t-butyldiphenylsilyl group, a salt or hydrate thereof, and a hydrate of the salt;

(48) the above compound in which n is 1, a salt or hydrate thereof, and a hydrate of the salt;

(49) the above compound in which each of $R^2$, $R^3$, $R^4$, $R^5$, $R^6$, and $R^7$ is a hydrogen atom, a salt or hydrate thereof, and a hydrate of the salt;

(50) the above compound in which $X^1$ is apartial structure of formula:

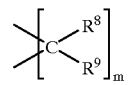

wherein $R^8$ and $R^9$ each independently represents a hydrogen atom or an alkyl group having 1 to 6 carbon atoms; and m represents an integer 1 or 2, a salt or hydrate thereof, and a hydrate of the salt;

(51) the above compound in which m is 1, a salt or hydrate thereof, and a hydrate of the salt;

(52) a process for preparing a quinolone compound characterized by comprising removing Q' from a compound of the following formula, a salt or hydrate thereof, or a hydrate of the salt:

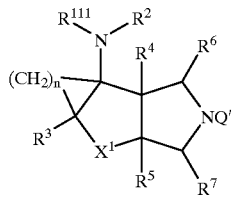

wherein $R^{111}$ represents a hydrogen atom, an alkyl group having 1 to 6 carbon atoms, or a protective group for amino group;

$R^2$ represents a hydrogen atom or an alkyl group having 1 to 6 carbon atoms;

in which the alkyl group as $R^{111}$ or $R^2$ may have one or more substituents selected from the group consisting of a hydroxyl group, a halogen atom, an alkylthio group having 1 to 6 carbon atoms, and an alkoxyl group having 1 to 6 carbon atoms;

$R^3$ represents a hydrogen atom, a hydroxyl group, a halogen atom, a carbamoyl group, an alkyl group having 1 to 6 carbon atoms, an alkoxyl group having 1 to 6 carbon atoms, or an alkylthio group having 1 to 6 carbon atoms, in which the alkyl group may have one or more substituents selected from the group consisting of a hydroxyl group, a halogen atom, and an alkoxyl group having 1 to 6 carbon atoms;

$R^4$ and $R^5$ each independently represents a hydrogen atom, a halogen atom, an alkyl group having 1 to 6 carbon atoms, or an alkoxyl group having 1 to 6 carbon atoms, in which the alkyl group may have one or more substituents selected from the group consisting of a hydroxyl group, a halogen atom, and an alkoxyl group having 1 to 6 carbon atoms;

$R^6$ and $R^7$ each independently represents a hydrogen atom or an alkyl group having 1 to 6 carbon atoms;

$X^1$ represents an oxygen atom, a sulfur atom, a partial structure:

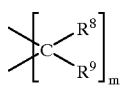

(wherein $R^8$ and $R^9$ each independently represents a hydrogen atom or an alkyl group having 1 to 6 carbon atoms; and m represents an integer 1 or 2) or a partial structure:

(wherein $R^{10}$ represents a hydrogen atom, a formyl group, an acyl group having 2 to 5 carbon atoms or an alkyl group having 1 to 6 carbon atoms);

n represents an integer 1 or 2; and

Q' represents a protective group for amino group, and reacting the resulting compound as obtained or, if desired, as isolated and purified with a compound represented by formula (III):

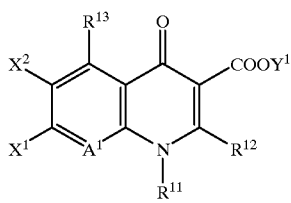

(III)

wherein $X^2$ represents a halogen atom or a hydrogen atom;

$X^4$ represents a fluorine atom, a chlorine atom, a bromine atom, a substituted or unsubstituted phenylsulfonyl group or a substituted or unsubstituted alkylsulfonyl group having 1 to 3 carbon atoms;

$Y^1$ represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms, a phenylalkyl group composed of an alkylene group having 1 to 6 carbon atoms and a phenyl group, or a boron-containing group represented by formula (IV):

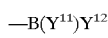 (IV)

(wherein $Y^{11}$ and $Y^{12}$ each represents a fluorine atom or an alkylcarbonyloxy group having 2 to 4 carbon atoms);

$R^{11}$ represents an alkyl group having 1 to 6 carbon atoms, an alkenyl group having 2 to 6 carbon atoms, a halogenoalkyl group having 1 to 6 carbon atoms, a substituted or unsubstituted cycloalkyl group having 3 to 6 carbon atoms, a substituted or unsubstituted aryl group, a substituted or unsubstituted heteroaryl group, an alkoxyl group having 1 to 6 carbon atoms or an alkylamino group having 1 to 6 carbon atoms;

$R^{12}$ represents a hydrogen atom or an alkylthio group having 1 to 6 carbon atoms;

$R^{12}$ and $R^{11}$ may be taken together with part of the mother skeleton to which they are bonded to form a cyclic structure that may contain a sulfur atom as a ring-constituting atom and an alkyl group having to 6 carbon atoms as a substituent;

$R^{13}$ represents a hydrogen atom, an amino group, a hydroxyl group, a thiol group, a halogenomethyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, in which the amino group may have one or two substituents selected from the group consisting of a formyl group, an alkyl group having 1 to 6 carbon atoms, and an acyl group having 2 to 5 carbon atoms; and $A^1$ represents a nitrogen atom or a partial structure represented by formula (II):

 (II)

(wherein $X^3$ represents a hydrogen atom, an amino group, a halogen atom, a cyano group, a halogenomethyl group, a halogenomethoxyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, in which the amino group may have one or two substituents selected from the group consisting of a formyl group, an alkyl group having 1 to 6 carbon atoms and an acyl group having 2 to 5 carbon atoms; and $X^3$ and $R^{11}$ may be taken together with part of the mother skeleton to which they are bonded to form a cyclic structure that may contain an oxygen atom, a nitrogen atom or a sulfur atom as a ring-constituting atom and an alkyl group having 1 to 6 carbon atoms as a substituent), or a compound represented by formula (V):

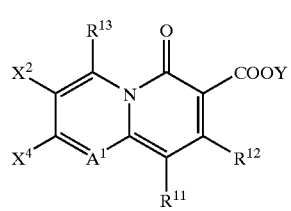 (V)

wherein $X^2$, $X^4$, $R^{11}$, $R^{12}$, $R^{13}$, $A^1$, and Y are as defined above, in the presence of a base, and if desired removing a protective group;

(53) a process for preparing a quinolone compound characterized by comprising reacting a compound represented by formula (VI), a salt or hydrate thereof, or a hydrate of the salt:

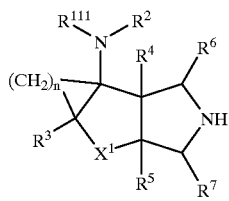
(VI)

wherein $R^{111}$ represents a hydrogen atom, an alkyl group having 1 to 6 carbon atoms or a protective group for amino group;

$R^2$ represents a hydrogen atom or an alkyl group having 1 to 6 carbon atoms;

in which the alkyl group as $R^{111}$ or $R^2$ may have one or more substituents selected from the group consisting of a hydroxyl group, a halogen atom, an alkylthio group having 1 to 6 carbon atoms, and an alkoxyl group having 1 to 6 carbon atoms;

$R^3$ represents a hydrogen atom, a hydroxyl group, a halogen atom, a carbamoyl group, an alkyl group having 1 to 6 carbon atoms, an alkoxyl group having 1 to 6 carbon atoms, or an alkylthio group having 1 to 6 carbon atoms, in which the alkyl group may have one or more substituents selected from the group consisting of a hydroxyl group, a halogen atom, and an alkoxyl group having 1 to 6 carbon atoms;

$R^4$ and $R^5$ each independently represents a hydrogen atom, a halogen atom, an alkyl group having 1 to 6 carbon atoms, or an alkoxyl group having 1 to 6 carbon atoms, in which the alkyl group may have one or more substituents selected from the group consisting of a hydroxyl group, a halogen atom, and an alkoxyl group having 1 to 6 carbon atoms;

$R^6$ and $R^7$ each independently represents a hydrogen atom or an alkyl group having 1 to 6 carbon atoms;

$X^1$ represents an oxygen atom, a sulfur atom, a partial structure:

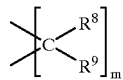

(wherein $R^8$ and $R^9$ each independently represents a hydrogen atom or an alkyl group having 1 to 6 carbon atoms; and m represents an integer 1 or 2) or a partial structure:

(wherein $R^{10}$ represents a hydrogen atom, a formyl group, an acyl group having 2 to 5 carbon atoms or an alkyl group having 1 to 6 carbon atoms); and n represents an integer 1 or 2, with a compound represented by formula (III):

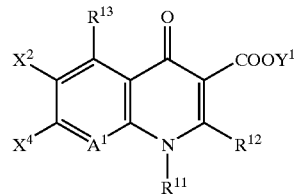
(III)

wherein $X^2$ represents a halogen atom or a hydrogen atom;

$X^4$ represents a fluorine atom, a chlorine atom, a bromine atom, a substituted or unsubstituted phenylsulfonyl group or a substituted or unsubstituted alkylsulfonyl group having 1 to 3 carbon atoms;

$Y^1$ represents a hydrogen atom, a phenyl group, an acetoxymethyl group, a pivaloyloxymethyl group, an ethoxycarbonyl group, a choline group, a dimethylaminoethyl group, a 5-indanyl group, a phthalidinyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms, a phenylalkyl group composed of an alkylene group having 1 to 6 carbon atoms and a phenyl group, or a boron-containing group represented by formula (IV):

—B(Y$^{11}$)Y$^{12}$ (IV)

(wherein $Y^{11}$ and $Y^{12}$ each represents a fluorine atom or an alkylcarbonyloxy group having 2 to 4 carbon atoms);

$R^{11}$ represents an alkyl group having 1 to 6 carbon atoms, an alkenyl group having 2 to 6 carbon atoms, a halogenoalkyl group having 1 to 6 carbon atoms, a substituted or unsubstituted cycloalkyl group having 3 to 6 carbon atoms, a substituted or unsubstituted aryl group, a substituted or unsubstituted heteroaryl group, an alkoxyl group having 1 to 6 carbon atoms or an alkylamino group having 1 to 6 carbon atoms;

$R^{12}$ represents a hydrogen atom or an alkylthio group having 1 to 6 carbon atoms;

$R^{12}$ and $R^{11}$ may be taken together with part of the mother skeleton to which they are bonded to form a cyclic structure that may contain a sulfur atom as a ring-constituting atom and an alkyl group having 1 to 6 carbon atoms as a substituent;

$R^{13}$ represents a hydrogen atom, an amino group, a hydroxyl group, a thiol group, a halogenomethyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, in which the amino group may have one or two substituents selected from the group consisting of a formyl group, an alkyl group having 1 to 6 carbon atoms, and an acyl group having 2 to 5 carbon atoms; and $A^1$ represents a nitrogen atom or a partial structure represented by formula (II):

(II)

(wherein $X^3$ represents a hydrogen atom, an amino group, a halogen atom, a cyano group, a halogenomethyl group, a halogenomethoxyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, in which the amino group may have one or two substituents selected from the group consisting of a formyl group, an alkyl group having 1 to 6 carbon atoms and an acyl group having 2 to 5 carbon atoms; and $X^3$ and $R^{11}$ may be taken together with part of the mother skeleton to which they are bonded to form a cyclic structure that may contain an oxygen atom, a nitrogen atom or a sulfur atom as a ring-constituting atom and an alkyl group having 1 to 6 carbon atoms as a substituent), or a compound represented by formula (V):

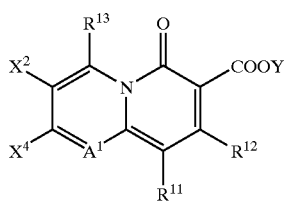

(V)

wherein $X^2$, $X^4$, $R^{11}$, $R^{12}$, $R^{13}$, $A^1$, and Y are as defined above, in the presence of a base, and if desired removing a protective group; and the like.

The compound represented by formula (I) according to the present invention is described with reference to the substituents thereof.

Substituents $R^1$ and $R^2$ each independently represents a hydrogen atom or an alkyl group having 1 to 6 carbon atoms which may be substituted with one or more substituents selected from the group consisting of a hydroxyl group, a halogen atom, an alkylthio group having 1 to 6 carbon atoms, and an alkoxyl group having 1 to 6 carbon atoms.

The alkyl group can be a straight-chain or branched alkyl group having 1 to 6 carbon atoms and preferably includes a methyl group, an ethyl group, an n-propyl group, and an isopropyl group.

Where the alkyl group has a hydroxyl group as a substituent, the alkyl group having 1 to 6 carbon atoms can be either straight or branched, and the hydroxyl group is preferably on the terminal carbon atom of the alkyl group. The hydroxyl-substituted alkyl group preferably contains up to 3 carbon atoms and preferably includes a hydroxymethyl group, a 2-hydroxyethyl group, a 2-hydroxypropyl group, and a 3-hydroxypropyl group.

Where the alkyl group has a halogen atom as a substituent, the alkyl group having 1 to 6 carbon atoms can be either straight or branched, and the halogen atom is preferably a fluorine atom. The number of fluorine substitution is any of from mono-substitution up to perfluoro-substitution. Examples of the halogen-substituted alkyl group are a monofluoromethyl group, a difluoromethyl group, a trifluoromethyl group, and a 2,2,2-trifluoroethyl group.

Where the alkyl group has an alkylthio group as a substituent, the alkyl group having 1 to 6 carbon atoms can be either straight or branched, and the alkylthio group can be a straight-chain or branched group having 1 to 6 carbon atoms. The alkylthio-substituted alkyl group preferably includes an alkylthiomethyl group, an alkylthioethyl group, and an alkylthiopropyl group, in which the alkylthio group preferably has up to 3 carbon atoms. Still preferred are a methylthiomethyl group, an ethylthiomethyl group, and a methylthioethyl group.

Where the alkyl group has an alkoxyl group as a substituent, the alkyl group having 1 to 6 carbon atoms can be either straight or branched, and the alkoxyl group can be a straight-chain or branched group having 1 to 6 carbon atoms. The alkoxy-substituted alkyl group preferably includes an alkoxymethyl group, an alkoxyethyl group, and an alkoxypropyl group, in which the alkoxyl group preferably contains up to 3 carbon atoms. Still preferred are a methoxymethyl group, an ethoxymethyl group, and a methoxyethyl group.

Substituent $R^3$ represents a hydrogen atom, a hydroxyl group, a halogen atom, a carbamoyl group, an alkyl group having 1 to 6 carbon atoms, an alkoxyl group having 1 to 6 carbon atoms, or an alkylthio group having 1 to 6 carbon atoms. The alkyl group may have one or more substituents selected from the group consisting of a hydroxyl group, a halogen atom, and an alkoxyl group having 1 to 6 carbon atoms.

The halogen atom is preferably a fluorine atom or a chlorine atom.

The alkyl group having 1 to 6 carbon atoms can be either straight or branched and preferably includes a methyl group, an ethyl group, an n-propyl group, and an isopropyl group.

The alkoxyl group having 1 to 6 carbon atoms can be either straight or branched and preferably includes a methoxyl group and an ethoxy group.

The alkylthio group having 1 to 6 carbon atoms can be either straight or branched and preferably includes a methylthio group and an ethylthio group.

Where a hydroxyl group is on the alkyl group having 1 to 6 carbon atoms as a substituent, the alkyl group can be either straight or branched, and the hydroxyl group is preferably on the terminal carbon atom of the alkyl group. The hydroxyl-substituted alkyl group having 1 to 6 carbon atoms preferably includes a hydroxymethyl group, a 2-hydroxyethyl group, and a 3-hydroxypropyl group.

The halogen atom of the halogen-substituted alkyl group is preferably a fluorine atom or a chlorine atom, with a fluorine atom being particularly preferred. The alkyl group can be either straight or branched.

Either alkyl moiety of the alkoxy-substituted alkyl group having 1 to 6 carbon atoms can be straight or branched. An alkoxymethyl group or an alkoxyethyl group is preferred. Still preferred are a methoxymethyl group, an ethoxymethyl group, and a 2-methoxyethyl group.

Substituents $R^4$ and $R^5$ each independently represents a hydrogen atom, a halogen atom, an alkyl group having 1 to 6 carbon atoms or an alkoxyl group having 1 to 6 carbon atoms, in which the alkyl group can have one or more substituents selected from the group consisting of a hydroxyl group, a halogen atom and an alkoxyl group having 1 to 6 carbon atoms.

The halogen atom is preferably a fluorine atom or a chlorine atom.

The alkyl group having 1 to 6 carbon atoms can be either straight or branched and preferably includes a methyl group, an ethyl group, an n-propyl group, and an isopropyl group.

The alkoxyl group having 1 to 6 carbon atoms can be either straight or branched and preferably includes a methoxyl group and an ethoxy group.

The hydroxyl-substituted alkyl group having 1 to 6 carbon atoms can be either straight or branched, and the hydroxyl group is preferably on the terminal carbon atom of the alkyl group. The hydroxyl-substituted alkyl group having 1 to 6 carbon atoms preferably includes a hydroxymethyl group, a 2-hydroxyethyl group, and a 3-hydroxypropyl group.

The halogen atom of the halogen-substituted alkyl group is preferably a fluorine atom or a chlorine atom, with a fluorine atom being particularly preferred. The alkyl group can be either straight or branched.

Either alkyl moiety of the alkoxy-substituted alkyl group having 1 to 6 carbon atoms can be straight or branched. An alkoxymethyl group or an alkoxyethyl group is preferred. Still preferred are a methoxymethyl group, an ethoxymethyl group, and a 2-methoxyethyl group.

Substituents $R^6$ and $R^7$ each independently represents a hydrogen atom or an alkyl group having 1 to 6 carbon atoms. The alkyl group having 1 to 6 carbon atoms can be straight or branched and preferably includes a methyl group, an ethyl group, an n-propyl group, and an isopropyl group.

$X^1$ represents an oxygen atom, a sulfur atom, a partial structure:

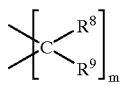

wherein $R^8$ and $R^9$ each independently represents a hydrogen atom or an alkyl group having 1 to 6 carbon atoms; and m represents an integer 1 or 2, or a partial structure:

wherein $R^{10}$ represents a hydrogen atom, a formyl group, an acyl group having 2 to 5 carbon atoms or an alkyl group having 1 to 6 carbon atoms.

$X^1$ is preferably the partial structure:

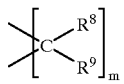

wherein
$R^8$, $R^9$, and m are as defined above.
$R^8$ and $R^9$ are preferably a hydrogen atom, and m is preferably 1.
n is preferably an integer 1 or 2, still preferably 1.
Q represents a partial structure represented by formula:

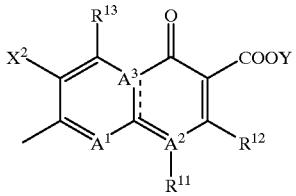

In the above formula, $A^2$ and $A^3$ each represents a nitrogen atom or a carbon atoms provided that $A^2$, $A^3$ and the carbon atom to which they are bonded are linked to form a partial structure:

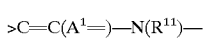

or a partial structure:

>N—C($A^1$=)=C($R^{11}$)—

Q preferably represents a condensed heterocyclic structure represented by formula:

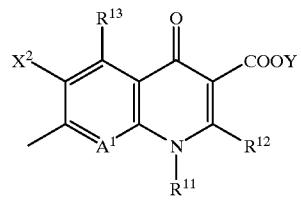

or formula:

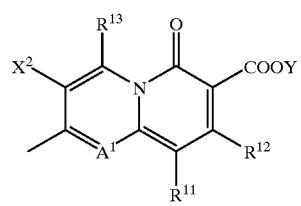

Substituent $R^{11}$ represents an alkyl group having 1 to 6 carbon atoms, an alkenyl group having 2 to 6 carbon atoms, a halogenoalkyl group having 1 to 6 carbon atoms, a substituted or unsubstituted cycloalkyl group having 3 to 6 carbon atoms, a substituted or unsubstituted aryl group, a substituted or unsubstituted heteroaryl group, an alkoxyl group having 1 to 6 carbon atoms or an alkylamino group having 1 to 6 carbon atoms.

The alkyl group having 1 to 6 carbon atoms is particularly preferably an ethyl group. The alkenyl group having 2 to 6 carbon atoms preferably includes a vinyl group and a 1-isopropenyl group. The halogenoalkyl group having 1 to 6 carbon atoms is preferably a 2-fluoroethyl group. The cycloalkyl group is preferably a cyclopropyl group. The substituent on the cycloalkyl group is preferably a halogen atom, which is preferably a fluorine atom.

The substituted or unsubstituted aryl group includes a phenyl group which may have 1 to 3 substituents selected from the group consisting of a halogen atom (e.g., fluorine, chlorine, and bromine), a hydroxyl group, an amino group, a nitro group, an alkyl group having 1 to 6 carbon atoms, an alkoxyl group having 1 to 6 carbon atoms, etc. The substituted or unsubstituted aryl group preferably includes a phenyl group, a 2-fluorophenyl group, a 4-fluorophenyl group, 2,4-difluorophenyl group, and a 2-fluoro-4-hydroxyphenyl group.

The heteroaryl group is a substituent derived from a 5-membered or 6-membered aromatic heterocyclic compound containing at least one hetero atom selected from a nitrogen atom, an oxygen atom and a sulfur atom and includes a pyridyl group and a pyrimidyl group. The substituents on the heteroaryl group preferably include an alkyl group and a halogen atom.

The alkoxyl group having 1 to 6 carbon atoms is preferably a methoxyl group. The alkylamino group having 1 to 6 carbon atoms is preferably a methylamino group.

Substituent $R^{11}$ is preferably a cycloalkyl group or a halogenocycloalkyl group, still preferably a cyclopropyl group or a 2-halogenocyclopropyl group, in which the halogen atom is preferably a fluorine atom.

Substituent $R^{12}$ represents a hydrogen atom or an alkylthio group having 1 to 6 carbon atoms, or $R^{11}$ and $R^{12}$ may be taken together with part of the mother skeleton (that is, the nitrogen atom to which $R^{11}$ is bonded and the carbon atom to which $R^{12}$ is bonded) to form a hydrocarbon ring structure. The ring formed may contain a sulfur atom in its ring. The ring may be substituted with an alkyl group having 1 to 6 carbon atoms. The ring can be a 4- to 6-membered ring and may be saturated, partially saturated or unsaturated. The condensed ring structure thus formed includes the following structures.

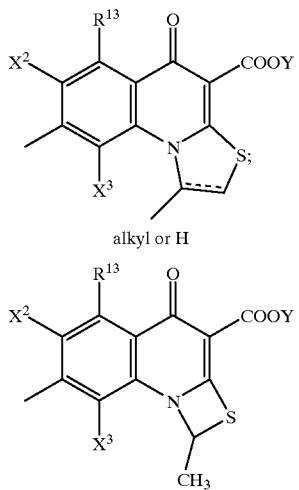

Substituent $X^2$ represents a halogen atom or a hydrogen atom. The halogen atom is preferably a fluorine atom. $X^2$ is preferably a fluorine atom or a hydrogen atom.

Substituent $R^{13}$ represents a hydrogen atom, an amino group, a hydroxyl group, a thiol group, a halogenomethyl group, an alkyl group having 1 to 6 carbon atoms, an alkenyl group having 2 to 6 carbon atoms, an alkynyl group having 2 to 6 carbon atoms or an alkoxyl group having 1 to 6 carbon atoms, in which the amino group may have one or two substituents selected from the group consisting of a formyl group, an alkyl group having 1 to 6 carbon atoms, and an acyl group having 2 to 5 carbon atoms.

The alkyl group having 1 to 6 carbon atoms can be straight or branched and preferably includes a methyl group, an ethyl group, an n-propyl group, and an isopropyl group. The alkenyl group having 2 to 6 carbon atoms can be straight or branched and preferably includes a vinyl group. The alkynyl group having 2 to 6 carbon atoms can be straight or branched and preferably includes an ethynyl group. The halogen of the halogenomethyl group is preferably a fluorine atom. The halogenomethyl group can have 1 to 3 halogen atoms. The alkoxyl group can have 1 to 6 carbon atoms and is preferably a methoxyl group.

Substituent $R^{13}$ is preferably a hydrogen atom, an alkyl group or an amino group, with a methyl group or an unsubstituted amino group being still preferred.

Where substituent $R^{13}$ is an amino group, a hydroxyl group or a thiol group, it may be protected with a commonly employed protective group.

Specific examples of the protective group include (substituted) alkoxycarbonyl groups, e.g., a t-butoxycarbonyl group and a 2,2,2-trichloroethoxycarbonyl group; (substituted) aralkyloxycarbonyl groups, e.g., a benzyloxycarbonyl group, a p-methoxybenzyloxycarbonyl group, and a p-nitrobenzyloxycarbonyl group; (substituted) acyl groups, e.g., an acetyl group, a methoxyacetyl group, a trifluoroacetyl group, a chloroacetyl group, a pivaloyl group, a formyl group, and a benzoyl group; (substituted) alkyl groups or (substituted) aralkyl groups, e.g., a t-butyl group, a benzyl group, a p-nitrobenzyl group, a p-methoxybenzyl group, and a triphenylmethyl group; (substituted) ether groups, e.g, a methoxymethyl group, a t-butoxymethyl group, a tetrahydropyranyl group, and a 2,2,2-trichloroethoxymethyl group; and (alkyl- and/or aralkyl)-substituted silyl groups, e.g., a trimethylsilyl group, an isopropyldimethylsilyl group, a t-butyldimethylsilyl group, a tribenzylsilyl group, and a t-butyldiphenylsilyl group. The term "substituted" in parentheses as used above means substituted or unsubstituted (hereinafter the same). The compounds having the thus protected substituent are particularly useful as an intermediate for synthesis.

Where $A^1$ is a partial structure of formula (II):

(II)

$X^3$ represents a hydrogen atom, an amino group, a halogen atom, a cyano group, a halogenomethyl group, a halogenomethoxyl group, an alkyl group having 1 to 6 carbon atoms, an alkenyl group having 2 to 6 carbon atoms, an alkynyl group having 2 to 6 carbon atoms, or an alkoxyl group having 1 to 6 carbon atoms, in which the amino group can have one or two substituents selected from the group consisting of a formyl group, an alkyl group having 1 to 6 carbon atoms, and an acyl group having 2 to 5 carbon atoms.

The alkyl group can be a straight-chain or branched alkyl group having 1 to 6 carbon atoms and preferably includes a methyl group, an ethyl group, an n-propyl group, and an isopropyl group. The alkenyl group can be a straight-chain or branched alkenyl group having 2 to 6 carbon atoms and preferably includes a vinyl group. The alkynyl group can be a straight-chain or branched alkenyl group having 2 to 6 carbon atoms and preferably includes an ethynyl group. The halogenomethyl group can contain 1 to 3 halogen atoms, and the halogen atom thereof is preferably a fluorine atom. The alkoxyl group has 1 to 6 carbon atoms and is preferably a methoxyl group. The halogenomethoxyl group can have 1 to 3 halogen atoms, and the halogen atom thereof is preferably a fluorine atom.

Of these substituents an alkyl group and an alkoxyl group are preferred. A methyl group and an ethyl group are still preferred. They are preferred particularly where Q is a partial structure of formula:

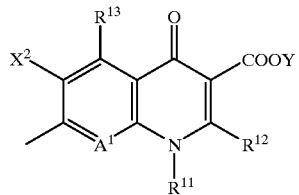

$X^3$ and $R^{11}$ may be taken together with part of the mother skeleton (that is, so as to include the carbon atom to which $X^3$ is bonded and the nitrogen atom to which $R^{11}$ is bonded) to form a hydrocarbon ring structure. The ring has a size of from 4- to 6-membered rings and may be saturated, partially saturated or unsaturated. The ring may contain an oxygen atom, a nitrogen atom or a sulfur atom as a ring-constituting atom. The ring may also have an alkyl group having 1 to 6 carbon atoms as a substituent. The condensed ring structure thus formed includes the following structures.

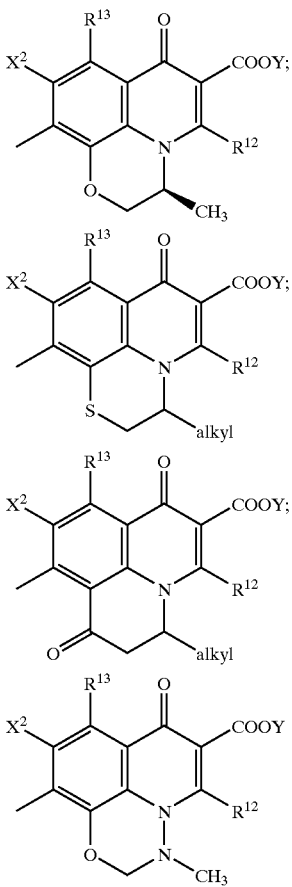

Of the condensed rings preferred is a 2,3-dihydro-7-oxo-7H-pyrido[1,2,3-de][1,4]benzoxazin-6-carboxylic acid-10-yl group, especially the 3(S)-methyl form thereof.

Q preferably represents a partial structure of formula:

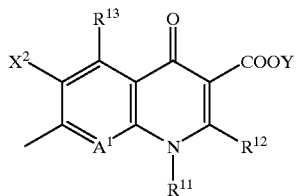

Q still preferably represents the above structure in which $A^1$ is the partial structure of formula (II).

Where Q is the partial structure shown above in which $A^1$ is the partial structure of formula (II), $R^{13}$ and $X^3$ are preferably selected to make such a combination that $R^{12}$ is an amino group, a hydrogen atom, a hydroxyl group or an alkyl group having 1 to 6 carbon atoms, and $X^3$ is an alkyl group having 1 to 6 carbon atoms, an alkoxyl group having 1 to 6 carbon atoms, a halogenomethoxyl group or a hydrogen atom. In a still preferred combination, $R^{13}$ is an amino group, a hydrogen atom, a hydroxyl group or a methyl group, and $X^3$ is a methyl group, a methoxyl group, a difluoromethoxyl group or a hydrogen atom. A particularly preferred combination is that $R^{13}$ is an amino group, a hydrogen atom, a hydroxyl group or a methyl group, and $X^3$ is a methyl group or a methoxyl group.

In the above cases, $X^2$ is preferably a fluorine atom.

Where $X^2$ and $X^3$ are each a halogen atom, $X^2$ is preferably a fluorine atom, and $X^3$ is preferably a fluorine atom or a chlorine atom.

Where Q is a partial structure represented by formula:

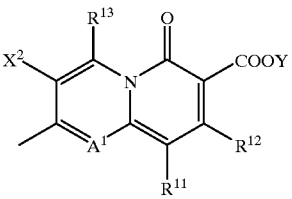

and $A^1$ is the partial structure of formula (II), $R^{13}$ and $X^3$ are preferably selected to make such a combination that $R^{12}$ is an amino group, a hydrogen atom, a hydroxyl group or an alkyl group having 1 to 6 carbon atoms, and $X^3$ is an alkyl group having 1 to 6 carbon atoms, an alkoxyl group having 1 to 6 carbon atoms, a halogenomethoxyl group or a hydrogen atom. In a still preferred combination, $R^{13}$ is an amino group, a hydrogen atom, a hydroxyl group or a methyl group, and $X^3$ is a methyl group, a methoxyl group, a fluorine atom, a chlorine atom, a difluoromethoxyl group or a hydrogen atom. A particularly preferred combination is that $R^{13}$ is an amino group, a hydrogen atom, a hydroxyl group or a methyl group, and $X^3$ is a methyl group or a methoxyl group.

Where $X^2$ and $X^3$ are each a halogen atom, $X^2$ is preferably a fluorine atom, and $X^3$ is preferably a fluorine atom or a chlorine atom.

The halogenocyclopropyl group as $R^{11}$ will hereinafter be described.

The substituent halogen atom includes a fluorine atom and a chlorine atom, with a fluorine atom being preferred.

It is particularly preferred that the halogen atom and the pyridonecarboxylic acid moiety be in a cis-configuration with respect to the cyclopropane ring.

The cis-2-halogenocyclopropyl moiety as $R^{11}$ makes a pair of antipodes by itself, each of which was observed to exhibit potent antimicrobial activity and high safety.

The compound of the present invention is characterized by having the substituent represented by the following structure:

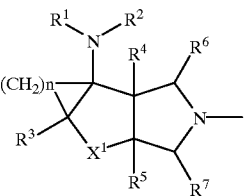

In this substituent, it is usual that the substituents —$N(R^1)R^2$ and $R^3$ are in a cis-configuration, so are the substituents $R^4$ and $R^5$. Therefore there are 4 isomers with respect to the condensed rings on which these substituents are.

Where the compound of formula (I) of the invention has such a structure that produces diastereomers, it is desirable to administer a compound comprising a pure diastereomer in administration to humans or animals. The language "a compound comprising a pure diastereomer" as used herein is construed as including not only a compound containing no other diastereomers at all but a compound containing other diastereomers to such an extent that the compound is regarded to be chemically pure. In other words, it is construed as meaning that other diastereomers may exist to some extent as long as the existence gives no substantial influence on physical constants or physiological activities.

The language "stereochemically pure" as used herein is intended to mean that a compound comprises only one of its stereoisomers ascribed to its asymmetric carbon atom. The latitude of the term "pure" in "pure diastereomer" also applies here.

The pyridonecarboxylic acid derivative of the present invention may have either a free form or a form of an acid addition salt or a carboxylic acid salt. Acid addition salts include inorganic acid salts, such as a hydrochloride, a sulfate, a nitrate, a hydrobromide, a hydroiodide, and a phosphate; and organic acid salts, such as an acetate, a metanesulfonate, a benzenesulfonate, a toluenesulfonate, a citrate, a maleate, a fumarate, and a lactate.

The carboxylic acid salts include inorganic salts and organic salts, such as alkali metal salts, e.g., a lithium salt, a sodium salt, and a potassium salt; alkaline earth metal salts, e.g., a magnesium salt and a calcium salt; an ammonium salt; a triethylamine salt, an N-methylglucamine salt, and a tris-(hydroxymethyl)aminomethane salt.

The free pyridonecarboxylic acid derivatives, acid addition salts thereof, and carboxylic acid salts thereof may be present as a hydrate.

On the other hand, quinolone derivatives with the carboxylic acid moiety thereof having an ester form are useful as an intermediate for synthesis or a pro-drug. For example, alkyl esters, benzyl esters, alkoxyalkyl esters, phenylalkyl esters, and phenyl esters are useful as intermediates for synthesis.

Esters which can be used as pro-drugs are those which are susceptible to an in vivo cleavage to form a free carboxylic acid, including an acetoxymethyl ester, a pivaloyloxymethyl ester, an ethoxycarbonyl ester, a choline ester, a dimethylaminoethyl ester, a 5-indanyl ester, a phthalidinyl ester, a 5-alkyl-2-oxo-1,3-dioxol-4-ylmethyl ester, and oxoalkyl esters, such as a 3-acetoxy-2-oxobutyl ester.

The compound of formula (I) can be prepared through various processes. A preferred process comprises reacting a compound represented by formula (III):

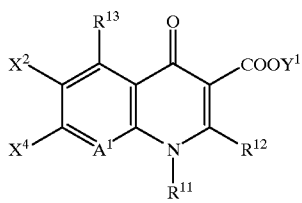

(III)

wherein $X^4$ represents a group functioning as a leaving group, such as a fluorine atom, a chlorine atom, a bromine atom, a substituted or unsubstituted phenylsulfonyl group, a substituted or unsubstituted alkylsulfonyl group having 1 to 3 carbon atoms, and the like; $Y^1$ has the same meaning as Y in formula (I) or represents a boron-containing group represented by formula (IV):

—B($Y^{11}$)$Y^{12}$ (IV)

(wherein $Y^{11}$ and $Y^{12}$ each represent a fluorine atom or an alkylcarbonyloxy group having 2 to 4 carbon atoms); and $R^{11}$, $R^{12}$, $R^{13}$, $A^1$, and $X^2$ are as defined in formula (I), or a compound represented by formula (V):

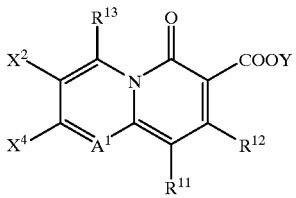

(V)

wherein $X^4$ represents a group functioning as a leaving group, such as a fluorine atom, a chlorine atom, a bromine atom, a substituted or unsubstituted phenylsulfonyl group, a substituted or unsubstituted alkylsulfonyl group having 1 to 3 carbon atoms, and the like; and $R^{11}$, $R^{12}$, $R^{13}$, $A^1$, $X^2$, and Y are as defined in formula (I), with a compound represented by formula (VI):

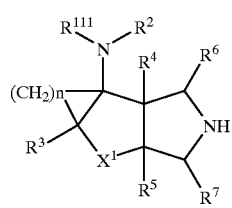

(VI)

wherein $R^{111}$ has the same meaning as $R^1$ in formula (I) or represents a protective group for amino group; and $R^2$, $R^3$, $R^4$, $R^5$, $R^6$, $R^7$, $X^1$, and n are as defined in formula (I), or an acid addition salt thereof.

The reaction is carried out with or without a solvent. The solvent which can be used in the reaction is not limited as long as it is inert under the reaction conditions. Suitable solvents include dimethyl sulfoxide, pyridine, acetonitrile, ethanol, chloroform, dimethylformamide, dimethylacetamide, N-methylpyrrolidone, tetrahydrofuran, water, and 3-methoxybutanol, and mixtures thereof.

It is advantageous to conduct the reaction in the presence of an acid acceptor, such as an inorganic base (e.g., an alkali metal or alkaline earth metal carbonate or hydrogencarbonate) or an organic base (e.g., triethylamine, pyridine or 1,8-diazabicycloundecene). The reaction is usually performed at room temperature to 200° C., preferably 25 to 150° C., for 0.5 to 48 hours. The reaction usually completes in about 0.5 to 2 hours.

Any protective group generally used in the art can be used as a protective group for amino group. Examples of useful protective groups include (substituted) alkoxycarbonyl groups, e.g., a t-butoxycarbonyl group and a 2,2,2-trichloroethoxycarbonyl group; (substituted) aralkyloxycarbonyl groups, e.g., a benzyloxycarbonyl group, a p-methoxybenzyloxycarbonyl group, and a p-nitrobenzyloxycarbonyl group; (substituted) acyl groups, e.g., an acetyl group, a methoxyacetyl group, a trifluoroacetyl group, a chloroacetyl group, a pivaloyl group, a formyl group, and a benzoyl group; (substituted) alkyl groups or (substituted) aralkyl groups, e.g., a t-butyl group, a benzyl group, a p-nitrobenzyl group, a p-methoxybenzyl group, and a triphenylmethyl group; (substituted) ether groups, e.g, a methoxymethyl group, a t-butoxymethyl group, a tetrahydropyranyl group, and a 2,2,2- trichloroethoxymethyl group; and (alkyl- and/or aralkyl)-substituted silyl groups, e.g., a trimethylsilyl group, an isopropyldimethylsilyl group, a t-butyldimethylsilyl group, a tribenzylsilyl group, and a t-butyldiphenylsilyl group.

The resulting compound in which Y or $Y^1$ is an alkyl group having 1 to 6 carbon atoms, an alkoxymethyl group having 2 to 7 carbon atoms or a phenylalkyl group composed of an alkylene group having 1 to 6 carbon atoms and a phenyl group can be converted to the corresponding carboxylic acid by treating under an acidic or basic condition commonly used for hydrolysis of carboxylic acid esters.

Where $Y^1$ is the structure of formula (IV), the compound obtained by the reaction between the compound (III) or the compound (V) and the compound (VI) can be converted to the corresponding carboxylic acid by treating under an acidic or basic condition.

When removal of a protective group is necessary, the protective group is removed under the condition properly selected for that protective group to give a desired compound represented by formula (I).

The compound of formula (VI) can be prepared by various processes. A preferred process is shown in Reference Examples hereinafter given, but the process is not limited thereto. The compound of formula (VI) is prepared by removing Q' from a compound represented by formula:

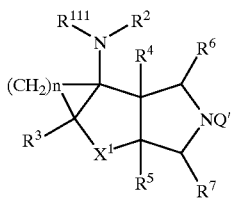

wherein $R^{111}$ is the same as $R^1$ as defined in formula (I) or represents a protective group for amino group; $R^2$, $R^3$, $R^4$, $R^5$, $R^6$, $R^7$, $X^1$, and n are as defined in formula (I); and Q' is a protective group for amino group, which can be selected from the group consisting of a (substituted) alkoxycarbonyl group, a (substituted) aralkyloxycarbonyl group, a (substituted) acyl group, a (substituted) alkyl group, a (substituted) aralkyl group, and a silyl group.

The above compound can exist in the form of a salt, ahydrate, or a hydrate of the salt. Acid addition salts include inorganic acid salts and organic acid salts. Examples of the inorganic acid salts are a hydrochloride, a sulfate, a nitrate, a hydrobromide, a hydroiodide, and a phosphate. Examples of the organic acid salts include sulfonates, such as a metanesulfonate, a benzenesulfonate, and a toluenesulfonate, and carboxylates, such as an acetate, a citrate, a maleate, a fumarate, and a lactate.

Where both $R^{111}$ and Q' represent a protective group for amino group, while they may be the same or different, it is advantageous for the preparation of the compound (I) that these protective groups are different so that they are released under the respective different reaction conditions.

The protective group for amino group as $R^{111}$ and Q' includes (substituted) alkoxycarbonyl groups, (substituted) aralkyloxycarbonyl groups, (substituted) acyl groups, (substituted) alkyl groups, (substituted) aralkyl groups, and silyl groups. Specific examples are (substituted) alkoxycarbonyl groups, e.g., a t-butoxycarbonyl group and a 2,2,2-trichloroethoxycarbonyl group; (substituted) aralkyloxycarbonyl groups, e.g., a benzyloxycarbonyl group, a p-methoxybenzyloxycarbonyl group, and a p-nitrobenzyloxycarbonyl group; (substituted) acyl groups, e.g., an acetyl group, a methoxyacetyl group, a trifluoroacetyl group, a chloroacetyl group, a pivaloyl group, a formyl group, and a benzoyl group; (substituted) alkyl groups or (substituted) aralkyl groups, e.g., a t-butyl group, a benzyl group, a p-nitrobenzyl group, a p-methoxybenzyl group, and a triphenylmethyl group; ether groups, e.g, a methoxymethyl group, a t-butoxymethyl group, a tetrahydropyranyl group, and a 2,2,2-trichloroethoxymethyl group; and substituted silyl groups, e.g., a trimethylsilyl group, an isopropyldimethylsilyl group, a t-butyldimethylsilyl group, a tribenzylsilyl group, and a t-butyldiphenylsilyl group.

In order to prepare the compound (I) by using the above-described compound having the protective group Q', it is necessary to remove the protective group Q' before reacting. In this case, the compound (VI) as obtained may be either subjected to the reaction with the compound (III) or (V) immediately after the protective group removal, usually in the same pot, or once isolated and then reacted.

Cis-2-fluorocyclopropylamine comprising a pure isomer, which is preferred for the synthesis of the compound of formula (I) comprising a pure isomer, can be synthesized by, for example, the process described in JP-A-2-231475. Synthesis of the compound of formula (I) comprising a pure isomer from the optically active cis-2-fluorocyclopropylamine derivative thus obtained can be carried out by, for example, the process described in JP-A-2-231475.

Examples of the compounds of the present invention are shown below.

10-{(1R,2R,6S)-1-Amino-4-azatricyclo[6.1.0.0$^{2,6}$]nonan-4-yl}-9-fluoro-2,3-dihydro-3-(S)-methyl-7-oxo-7H-pyrido[1.2.3-de][1,4]benzoxazine-6-carboxylic acid, 8-amino-10-{(1R,2R,6S)-1-amino-4-azatricyclo[6.1.0.0$^{2,6}$]nonan-4-yl}-9-fluoro-2,3-dihydro-3-(S)-methyl-7-oxo-7H-pyrido[1.2.3-de][1,4]benzoxazine-6-carboxylic acid, 5-amino-7-{(1R,2R,6S)-1-amino-4-azatricyclo[6.1.0.0$^{2,6}$]nonan-4-yl}-6-fluoro-1-[2-(S)-fluoro-1-(R)-cyclopropyl]-8-methyl-1,4-dihydro-4-oxoquinoline-3-carboxylic acid, 5-amino-7-{(1R,2R,6S)-1-amino-4-azatricyclo[6.1.0.0$^{2,6}$]nonan-4-yl}-6-fluoro-1-[2-(S)-fluoro-1-(R)-cyclopropyl]-8-methoxy-1,4-dihydro-4-oxoquinoline-3-carboxylic acid, 7-{(1R,2R,6S)-1-amino-4-azatricyclo[6.1.0.0$^{2,6}$]nonan-4-yl}-6-fluoro-1-[2-(S)-fluoro-1-(R)-cyclopropyl]-8-methoxy-1,4-dihydro-4-oxoquinoline-3-carboxylic acid, 7-{(1R,2R,6S)-1-amino-4-azatricyclo[6.1.0.0$^{2,6}$]nonan-4-yl}-6-fluoro-1-[2-(S)-fluoro-1-(R)-cyclopropyl]-8-methyl-1,4-dihydro-4-oxoquinoline-3-carboxylic acid, 7-{(1R,2R,6S)-1-amino-4-azatricyclo[6.1.0.0$^{2,6}$]nonan-4-yl}-6-fluoro-1-[2-(S)-fluoro-1-(R)-cyclopropyl]-1,4-dihydro-4-oxo-1,8-naphthridine-3-carboxylic acid, 8-{(1R,2R,6S)-1-amino-4-azatricyclo[6.1.0.0$^{2,6}$]nonan-4-yl}-1-cyclopropyl-7-fluoro-9-methyl-4-oxo-4H-quinolizine-3-carboxylic acid, and 10-{(1R,2R,6S)-1-amino-4-azatricyclo[6.1.0.0$^{2,6}$]nonan-4-yl}-9-fluoro-3-(S)-methyl-2H,3H,6H-oxopyrano[2,3,4-IJ]quinolizine-5-carboxlic acid.

The structures of these specific compounds are shown below.

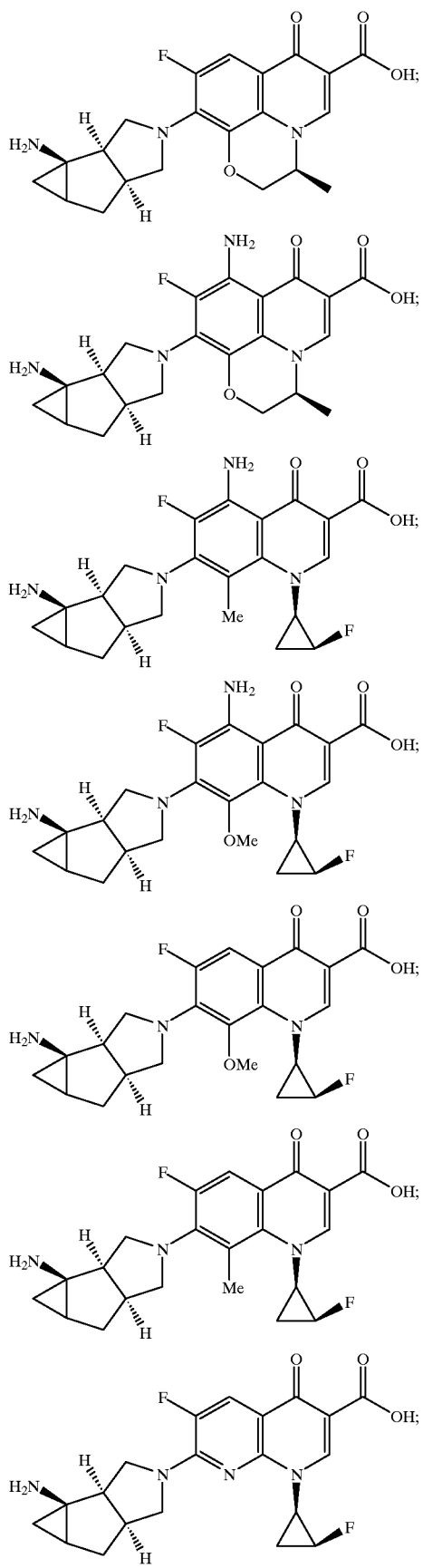

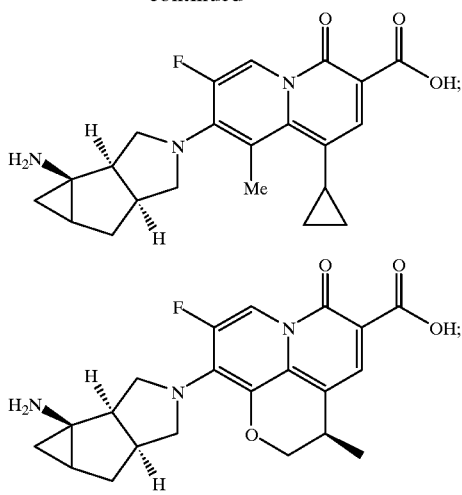

The compounds of the present invention have potent antimicrobial activity and are therefore useful as drugs for humans, animals or fishes, agricultural chemicals, or food preservatives.

For use as drugs for humans, the dose of the compound is in the range of from 50 mg to 1 g, preferably from 100 mg to 300 mg, per day for an adult.

For veterinary use, the dose is generally in the range of from 1 to 200 mg, preferably from 5 to 100 mg, per kg of body weight per day while varying depending on the purpose of administration (for therapy or for prevention), the kind and size of the animal, the kind of the pathogenic bacterium and the severity of infection.

The above-mentioned daily dose is given once a day or in 2 to 4 divided doses per day. If necessary, a daily dose may exceed the above-specified upper limit.

The compounds according to the invention are active on a broad range of microorganisms causing various infectious diseases and effective to prevent, alleviate or cure diseases caused by these pathogens.

Examples of bacteria or bacterium-like microorganisms on which the compounds of the invention are effective include Staphylococcus, *Streptococcus pyogenes*, hemolytic streptococcus, Enterococcus, *Streptococcus pneumoniae*, peptostreptococcus, gonococcus, *Escherichia coli*, Citrobacter, Shigella, *Klebsiella pneumoniae,* Enterobacter, Serratia, Proteus, *Pseudomonas aeruginosa, Haemophilus influenzae*, Acinetobacter, Campylobacter, and *Chlamydozoon trachomatis.*

Diseases which are caused by these pathogens include folliculitis, furuncle, carbuncle, erysipelas, phlegmon, lymphangitis/lymphadenitis, felon, subcutaneous abscess, spiradenitis, acne agminate, infectious atheroma, perianal abscess, mastadenitis, superficial secondary infections after trauma, burn or surgery trauma, pharyngolaryngitis, acute bronchitis, tonsillitis, chronic bronchitis, bronchiectasis, diffuse panbronchiolitis, secondary infections of chronic respiratory diseases, pneumonia, pyelonephritis, cystitis, prostatitis, epididymitis, gonococcal urethritis, non-gonococcal urethritis, cholecystitis, cholangitis, bacillary dysentery, enteritis, adnexitis, intrauterine infections, bartholinitis, blepharitis, hordeolum, dacryocystitis, tarsadenitis, keratohelcosis, otitis media, sinusitis, paradentosis, pericoronitis, gnathitis, peritonitis, endocarditis, septicemia, meningitis, and skin infections.

The compounds of the invention are also effective on various microorganisms causing veterinary infectious diseases, such as those belonging to the genera Escherichia, Salmonella, Pasteurella, Haemophilus, Bordetella, Staphylococcus, and Mycoplasma. Illustrative examples of the diseases include those of fowl, such as colibacillosis, pullorum disease, avian paratyphosis, fowl cholera, infectious coryza, staphylomycosis, and mycoplasmosis; those of pigs, such as colibacillosis, salmonellosis, pasteurellosis, hemophilus infections, atrophic rhinitis, exudative epidermitis, and mycoplasmosis; those of cattle, such as colibacillosis, salmonellosis, hemorrhagic septicemia, mycoplasmosis, bovine contagious pleuropneumonia, and bovine mastitis; those of dogs, such as colisepsis, salmonellosis, hemorrhagic septicemia, pyometra, and cystitis; those of cats, such as exudative pleurisy, cystitis, chronic rhinitis, and hemophilus infections; and those of kittens, such as bacterial diarrhea and mycoplasmosis.

Dosage forms of antimicrobial preparations containing the compound of the present invention are appropriately selected according to the administration route and can be prepared by conventional preparation methods. Examples of dosage forms for oral administration include tablets, powders, granules, capsules, solutions, syrups, elixirs, and oily or aqueous suspensions.

Injectable preparations may contain adjuvants, such as stabilizers, antiseptics, and solubilizers. The injectable solution which may contain these adjuvants may be put into a container and solidified by, for example, lyophilization to prepare a solid preparation, which is dissolved on use. The container may contain either a single dose or multiple doses.

Preparations for external application include solutions, suspensions, emulsions, ointments, gels, creams, lotions, and sprays.

Solid preparations may contain, in addition to the active compound, pharmaceutically acceptable additives. For example, the active compound is mixed with additives selected according to necessity from among fillers, extenders, binders, disintegrators, absorption accelerators, wetting agents, and lubricants and formulated into solid preparations.

Liquid preparations include solutions, suspensions, and emulsions. They may contain adjuvants, such as suspending agents, emulsifiers, and so forth.

The compound can be administered to animals orally either directly or by mixing into feedstuff, or in a dissolved form directly given to animals or by mixing into water or feedstuff or non-orally by injection.

For veterinary use, the compound can be formulated into powders, fine granules, soluble powders, syrups, solutions, and injections according to the customary methods in the art.

Formulation Examples are shown below.

FORMULATION EXAMPLE 1

| Capsules: | |
| --- | --- |
| Compound of Example 3 | 100.0 mg |
| Corn starch | 23.0 mg |
| CMC-Ca | 22.5 mg |
| Hydroxymethyl cellulose | 3.0 mg |
| Magnesium stearate | 1.5 mg |
| Total: | 150.0 mg |

FORMULATION EXAMPLE 2

| Solution: | |
| --- | --- |
| Compound of Example 2 | 1 to 10 g |
| Acetic acid or sodium hydroxide | 0.5 to 2 g |
| Ethyl p-hydroxybenzoate | 0.1 g |
| Purified water | 88.9 to 98.4 g |
| Total: | 100 g |

FORMULATION EXAMPLE 3

| Powder for Mixing into Feed: | |
| --- | --- |
| Compound of Example 2 | 1 to 10 g |
| Corn starch | 89.5 to 98.5 g |
| Light anhydrous silicic acid | 0.5 g |
| Total: | 100 g |

Best Embodiments for Carrying out the Invention

The present invention will further be illustrated by way of Examples and Reference Examples, but the present invention should not be construed as being limited thereto.

Reference Example 1

7-Benzyl-2-oxo-7-azabicyclo[3.3.0]octane

Trifluoroacetic acid (385 μl) was added to a solution of 2-cyclopenten-1-one (10.1 ml, 120 mmol) and benzylbutoxymethyltrimethylsilylmethylamine (41.9 g, 150 mmol) in dichloromethane (300 ml) at room temperature, followed by stirring for 16 hours. The dichloromethane was evaporated, and a saturated aqueous solution of sodium hydrogencarbonate was added to the residue. The mixture was extracted with ethyl acetate. The organic layer was washed with a saturated sodium chloride aqueous solution and dried over anhydrous sodium sulfate. The solvent was evaporated, and the residue was purified by silica gel column chromatography (n-hexane:ethyl acetate=1:1) to give 24.92 g (115.7 mmol, 96%) of the title compound as a yellow oily substance. $^1$H-NMR (400 MHz, CDCl$_3$) δ: 1.75–1.83 (1H, m), 2.08–2.18 (1H, m), 2.24–2.32 (1H, m), 2.37–2.49 (2H, m), 2.59–2.64 (1H, m), 2.67 (1H, dd, J=2.5, 9.5 Hz), 2.85–2.93 (1H, m), 3.04 (1H, dd, J=1.5, 9.5 Hz), 3.48 (1H, d, J=13.0 Hz), 3.61 (1H, d, J=13.0 Hz), 7.21–7.31 (5H, m)

Reference Example 2

7-Benzyloxycarbonyl-2-oxo-7-azabicyclo[3.3.0]octane

Benzyloxycarbonyl chloride (5.14 ml, 36.0 mmol) was added dropwise to a solution of 7-benzyl-2-oxo-7-azabicyclo [3.3.0]octane (5.20 g, 24.2 mmol) in dichloromethane (50 ml) under cooling with ice, followed by stirring at room temperature for 24 hours. The mixture was again cooled with ice, and benzyloxycarbonyl chloride (5.14 ml, 36.0 mmol) was added thereto dropwise. After removing the solvent by evaporation, the residue was purified by silica gel column chromatography (n-hexane:ethyl acetate=1:1) to give 4.52 g (17.4 mmol, 72%) of the title compound as acolorless oily substance. $^1$H-NMR (400 MHz, CDCl$_3$) δ: 1.80–1.90 (1H, m), 2.12–2.22 (1H, m), 2.35–2.39 (2H, m), 2.76 (1H, dt, J=3.5, 8.5 Hz), 3.01–3.11 (1H, m), 3.16–3.26 (1H, m), 3.61–3.66 (1H, m), 3.69–3.78 (1H, m), 5.11–5.12 (2H, m), 7.29–7.38 (5H, m)

Reference Example 3
2-(N-Benzyl-N-benzyloxycarbonyl)amino-7-benzyloxycarbonyl-7-azabicyclo[3.3.0]oct-2-ene Benzylamine (2.08 ml, 19.0 mmol) was added dropwise to a mixture of 7-benzyloxycarbonyl-2-oxo-7-azabicyclo[3.3.0]octane (4.51 g, 17.4 mmol), anhydrous magnesium sulfate (3.5 g), and tetrahydrofuran (50 ml) under cooling with ice. After stirring the mixture for 1 hour, the insoluble matter was removed by filtration, and the filtrate was concentrated. The resulting residue was dissolved in benzene (60 ml), and triethylamine (4.88 ml, 35.0 mmol) was added to the solution. To the mixture was further added triphosgene (2.67 g, 9.0 mmol) under cooling with ice, followed by stirring at room temperature for 1 hour. The insoluble matter was removed by Celite filtration, and the filtrate was concentrated. The residue was dissolved in tetrahydrofuran (30 ml), and the solution was added dropwise to a tetrahydrofuran (50 ml) solution of benzyloxysodium (25.0 mmol) under ice-cooling, followed by stirring at room temperature for 30 minutes. A saturated ammonium chloride aqueous solution was added thereto under cooling with ice, and the mixture was extracted with ethyl acetate. The extract was washed successively with water and a saturated sodium chloride aqueous solution and dried over anhydrous sodium sulfate. After the solvent was removed by evaporation, the residue was purified by silica gel column chromatography (n-hexane:ethyl acetate=1:1) to give 2.22 g (10.3 mmol, 59%) of the title compound as a colorless oily substance.

Reference Example 4
1-(N-Benzyl-N-benzyloxycarbonyl)amino-4-benzyloxycarbonyl-4-azatricyclo[6.1.0.0$^{2,6}$]nonane Diethylzinc (1 M n-hexane solution; 20 ml, 20.0 mmol) was added to a solution of 2-(N-benzyl-N-benzyloxycarbonyl)amino-7-benzyloxycarbonyl-7-azabicyclo[3.3.0]oct-2-ene (920 mg, 1.91 mmol) in dichloromethane (50 ml) at room temperature, and diiodomethane (3.06 ml, 38.0 mmol) was added thereto dropwise. After stirring the mixture for 16 hours, a saturated ammonium chloride aqueous solution was added thereto, and the mixture was extracted with ethyl acetate. The organic layer was washed successively with a sodium thiosulfate aqueous solution and a saturated sodium chloride aqueous solution, and dried over anhydrous sodium sulfate. After the solvent was evaporated, the residue was purified by silica gel column chromatography (n-hexane:ethyl acetate=3:1) to give 678 mg (1.36 mmol, 71%) of the title compound as a colorless oily substance.

Reference Example 5
1-Amino-4-azatricyclo[6.1.0.0$^{2,6}$]nonane

To a solution of 1-(N-benzyl-N-benzyloxycarbonyl)amino-4-benzyloxycarbonyl-4-azatricyclo-[6.1.0.0$^{2,6}$]nonane (675 mg, 1.36 mmol) in methanol (50 ml) was added 20% palladium hydroxide-on-carbon (500 mg), and the mixture was vigorously stirred in a hydrogen atmosphere for 120 hours. The insoluble matter was removed by Celite filtration, and the filtrate was concentrated to give the title compound as a crude colorless oily substance.

EXAMPLE 1
5-Amino-7-(1-amino-4-azatricyclo[6.1.0.0$^{2,6}$]-nonan-4-yl)-1-cyclopropyl-6,8-difluoro-1,4-dihydro-4-oxoquinoline-3-carboxylic Acid 5-Amino-1-cyclopropyl-6,7,8-trifluoro-1,4-dihydro-4-oxoquinoline-3-carboxylic acid (298 mg, 1.0 mmol) was added to a solution of 1-amino-4-azatricyclo[6.1.0.0$^{2,6}$]nonane (206 mg, 1.36 mmol) and triethylamine (418 µl, 3.0 mmol) in acetonitrile (10 ml) at room temperature, and the mixture was heated under reflux for 16 hours. After cooling to room temperature, the acetonitrile was evaporated. To the residue was added an aqueous hydrochloric acid solution, followed by washing with chloroform. The aqueous layer was made alkaline with an aqueous sodium hydroxide solution and washed with chloroform. The aqueous layer was adjusted to pH 7.5 with an aqueous hydrochloric acid solution and extracted with chloroform. The extract was dried over anhydrous sodium sulfate, and the solvent was removed by evaporation. The residue was recrystallized from ethanol. Recrystallization from 2-propanol gave 21 mg of the title compound as yellow crystals.

$^1$H-NMR (400 MHz, 0.1N-NaOD) δ: 0.06–0.08 (2H, m), 0.30–0.62 (4H, m), 0.73–0.75 (1H, m), 1.17–1.21 (1H, m), 1.27–1.36 (1H, m), 1.72–1.77 (1H, m), 2.10–2.17 (1H, m), 2.73–2.77 (1H, m), 3.00–3.08 (1H, m), 3.23–3.31 (3H, m), 7.68 (1H, s)

Melting point: 197–202° C. (decomposition)

Elemental analysis for $C_{21}H_{22}F_2N_4O_3 \cdot 5H_2O$: Calcd.: C, 59.28; H, 5.44; N, 13.17 Found: C, 59.48; H, 5.40; N, 12.90

Reference Example 6
(1R,5S)-7-Benzyl-2-oxo-7-azabicyclo[3.3.0]oct-3-ene

Trifluoroacetic acid (154 µl) was added to a solution of (4R)-4-t-butyldimethylsilyloxy-2-cyclopenten-1-one (5.79 g, 27.3 mmol) and benzylbutoxymethyltrimethylsilylmethylamine (15.4 g, 55.0 mmol) in dichloromethane (100 ml) at room temperature, followed by stirring for 20 minutes. A saturated sodium hydrogencarbonate aqueous solution was added to the reaction mixture, and the mixture was extracted with ethyl acetate. The organic layer was washed with a saturated sodium chloride aqueous solution and dried over anhydrous sodium sulfate. After removing the solvent by evaporation, the residue was purified by silica gel column chromatography (n-hexane:ethyl acetate=1:1) to give 4.21 g (19.7 mmol, 72%) of the title compound as a colorless oily substance. (1R,4R,5S)-7-Benzyl-4-t-butyldimethylsilyloxy-2-oxo-7-azabicyclo[3.3.0]octane was also obtained as a mixture with t-butyldimethylsilanol (3.10 g). The resulting mixture (3.10 g) of (1R,4R,5S)-7-benzyl-4-t-butyldimethylsilyloxy-2-oxo-7-azabicyclo[3.3.0]octane and t-butyldimethylsilanol was dissolved in tetrahydrofuran (30 ml), and a 1 M tetrahydrofuran solution (15 ml) of tetrabutylammonium fluoride was added thereto under cooling with ice, followed by stirring at room temperature for 20 minutes. The reaction mixture was poured into water and extracted with ethyl acetate. The organic layer was washed with a saturated sodium chloride aqueous solution and dried over anhydrous sodium sulfate. The solvent was removed by evaporation, and the residue was purified by silica gel column chromatography (n-hexane:ethyl acetate=1:1) to give 1.57 g (7.34 mmol) of the title compound as a colorless oily substance.

$^1$H-NMR (400 MHz, CDCl$_3$) δ: 2.32 (1H, t, J=9.0 Hz), 2.37 (1H, t, J=9.0 Hz), 2.72–2.76 (1H, m), 2.78 (1H, d J=9.5 Hz), 3.10 (1H, d, J=9.5 Hz), 3.36–3.41 (1H, m), 3.51 (1H, d, J=13.0 Hz), 3.60 (1H, d, J=13.0 Hz), 6.24 (1H, dd, J=1.0, 5.5 Hz), 7.20–7.30 (5H, m), 7.56 (1H, dd, J=2.5, 5.5 Hz) (1R,4R,5S)-7-Benzyl-4-t-butyldimethylsilyloxy-2-oxo-7-azabicyclo[3.3.0]octane $^1$H-NMR (400 MHz; CDCl$_3$) δ: –0.01 (3H, s), 0.00 (3H, s), 0.81 (9H, s), 2.23 (1H, ddt, J=1.5, 3.0, 17.0 Hz), 2.33–2.38 (2H, m), 2.57 (1H, dd, J=5.5, 17.0 Hz), 2.71–2.75 (3H, m), 3.04 (1H, d, J=9.0 Hz), 3.39 (1H, d, J=13.0 Hz), 3.60 (1H, d, J=13.0 Hz), 4.18–4.20 (1H, m), 7.18–7.27 (5H, m)

Reference Example 7
(1R,5S)-7-Benzyl-2-oxo-7-azabicyclo[3.3.0]octane

5% Rhodium-on-alumina (700 mg) was added to a solution of (1R,5S)-7-benzyl-2-oxo-7-azabicyclo[3.3.0]oct-3-ene (1.57 g, 7.34 mmol) in ethyl acetate (50 ml), and the mixture was vigorously stirred in a hydrogen atmosphere for 3.5 hours. The insoluble matter was removed by Celite filtration, and the filtrate was concentrated. The residue was purified by silica gel column chromatography (n-hexane:ethyl acetate=1:1) to give 1.31 g (6.10 mmol, 83%) of the title compound as a colorless oily substance.

$^1$H-NMR (400 MHz, CDCl$_3$) δ: 1.75–1.83 (1H, m), 2.08–2.18 (1H, m), 2.24–2.32 (1H, m), 2.37–2.49 (2H, m), 2.59–2.64 (1H, m), 2.67 (1H, dd, J=2.5, 9.5 Hz), 2.85–2.93 (1H, m), 3.04 (1H, dd, J=1.5, 9.5 Hz), 3.48 (1H, d, J=13.0 Hz), 3.61 (1H, d, J=13.0 Hz), 7.21–7.31 (5H, m)

Reference Example 8
(1R,5S)-7-Benzyloxycarbonyl-2-oxo-7-azabicyclo[3.3.0]octane A solution of benzyloxycarbonyl chloride (4.28 ml, 30.0 mmol) in dichloromethane (15 ml) was added dropwise to a solution of (1R,5S)-7-benzyl-2-oxo-7-azabicyclo[3.3.0]octane (1.31 g, 6.10 mmol) in dichloromethane (20 ml) while cooling with ice, and the mixture was stirred at room temperature for 16 hours. The solvent was removed by evaporation, and the residue was purified by silica gel column chromatography (n-hexane:ethyl acetate=1:1) to give 1.36 g (5.24 mmol, 86%) of the title compound as a colorless oily substance.

$^1$H-NMR (400 MHz, CDCl$_3$) δ: 1.80–1.90 (1H, m), 2.12–2.22 (1H, m), 2.35–2.39 (2H, m), 2.76 (1H, dt, J=3.5, 8.5 Hz), 3.01–3.11 (1H, m), 3.16–3.26 (1H, m), 3.61–3.66 (1H, m), 3.69–3.78 (1H, m), 5.11–5.12 (2H, m), 7.29–7.38 (5H, m)

Reference Example 9
(1'R,5'S)-Spiro[7'-benzyloxycarbonyl-7'-azabicyclo[3.3.0]octane-1,2'-2,5-dioxolane]

Ethylene glycol (4.46 ml, 80.0 mmol) and p-toluenesulfonic acid monohydrate (190.2 mg, 1.0 mmol) were added to a solution of (1R,5S)-7-benzyloxycarbonyl-2-oxo-7-azabicyclo[3.3.0]octane (8.27 g, 31.9 mmol) in benzene (100 ml), and the mixture was refluxed for 3 hours while removing water produced with a Dean-Stark apparatus. After cooling to room temperature, the reaction mixture was poured into a saturated aqueous solution of sodium hydrogencarbonate and extracted with ethyl acetate. The organic layer was washed successively with water and a saturated sodium chloride aqueous solution and dried over anhydrous sodium sulfate. The solvent was evaporated to give 9.71 g (quantitative) of the title compound as a crude colorless oily substance.

$^1$H-NMR (400 MHz, CDCl$_3$) δ: 1.45–1.53 (1H, m), 1.75–1.83 (1H, m), 1.89–2.01 (2H, m), 2.61 (1H, dt, J=5.5, 9.0 Hz), 2.74–2.84 (1H, m), 3.23–3.33 (1H, m), 3.44–3.62 (3H, m), 3.90–3.92 (4H, m), 5.11–5.14 (2H, m), 7.28–7.37 (5H, m).

Reference Example 10
(1'R,5'S)-Spiro[7'-azabicyclo[3.3.0]octane-1,2'-2,5-dioxolane]

10% Palladium-on-carbon (2.0 g) was added to a solution of the crude (1'R,5'S)-spiro[7'-benzyloxycarbonyl-7'-azabicyclo[3.3.0]octane-1,2'-2,5-dioxolane] (9.71 g, 31.9 mmol) in methanol (200 ml), and the mixture was vigorously stirred in a hydrogen atmosphere for 2 hours. The insoluble matter was removed by Celite filtration. Concentration of the residue gave a crude product of the title compound (5.17 g, 30.6 mmol, 95%) as a colorless oily substance.

$^1$H-NMR (400 MHz, CDCl$_3$) δ: 1.26–1.34 (1H, m), 1.63–1.69 (1H, m), 1.73–1.80 (1H, m), 1.93 (1H, dq, J=7.5, 12.5 Hz), 2.48–2.53 (1H, m), 2.62–2.71 (2H, m), 2.76 (1H, dd, J=8.0, 12.0 Hz), 2.92 (1H, dd, J=7.0, 11.0 Hz), 3.00 (1H, dd, J=4.0, 12.0 Hz), 3.88–3.95 (4H, m)

Reference Example 11
(1'R,5'S)-Spiro[7'-p-anisoyl-7'-azabicyclo[3.3.0]octane-1,2'-2,5-dioxolane]

p-Anisoyl chloride (6.82 g, 40.0 mmol) was added to a solution of (1'R,5'S)-spiro[7'-azabicyclo[3.3.0]octane-1,2'-2,5-dioxolane] (5.17 g, 30.6 mmol) and triethylamine (6.97 ml, 50.0 mmol) in dichloromethane (100 ml) under ice-cooling. The mixture was stirred at room temperature for 1 hour, and the reaction mixture was poured into a 10% aqueous citric acid solution and extracted with ethyl acetate. The organic layer was washed successively with a saturated aqueous solution of sodium hydrogencarbonate and a saturated aqueous solution of sodium chloride and dried over anhydrous sodium sulfate. The solvent was evaporated, and the residue was purified by silica gel column chromatography (chloroform:methanol=50:1) to give 9.02 g (29.7 mmol, 93%) of the title compound as a colorless oily substance.

Reference Example 12
(1R,5S)-7-p-Anisoyl-2-oxo-7-azabicyclo[3.3.0]octane (1'R,5'S)-Spiro[7'-anisoyl-7'-azabicyclo[3.3.0]octane-1,2'-2,5-dioxolane] (9.02 g, 29.7 mmol) was dissolved in 80% acetic acid (150 ml), and the solution was refluxed for 2.5 hours. After cooling to room temperature, the acetic acid was removed by evaporation. To the residue was added a saturated aqueous solution of sodium hydrogencarbonate, and the mixture was extracted with ethyl acetate. The organic layer was washed with a saturated sodium chloride aqueous solution and dried over anhydrous sodium sulfate. Removal of the solvent by evaporation gave 7.91 g (quantitative) of the title compound as a crude colorless oily substance.

Reference Example 13
(1R,5S)-2-(N-Benzyl-N-benzyloxycarbonyl)amino-7-p-anisoyl-7-azabicyclo[3.3.0]oct-2-ene Benzylamine (3.82 ml, 35.0 mmol) was added dropwise to a mixture of the crude (1R,5S)-7-p-anisoyl-2-oxo-7-azabicyclo[3.3.0]octane (7.91 g, 29.7 mmol), anhydrous magnesium sulfate (10 g), andtetrahydrofuran (100 ml) under cooling with ice, followed by stirring for 1 hour. The insoluble matter was removed by filtration, and the filtrate was concentrated. The residue was dissolved in benzene (100 ml), and triethylamine (6.27 ml, 45.0 mmol) was added thereto. To the mixture was further added triphosgene (4.45 g, 15.0 mmol) under ice-cooling, and the mixture was stirred at room temperature for 1 hour. The insoluble matter was removed by Celite filtration, and the filtrate was concentrated. The residue was dissolved in tetrahydrofuran (30 ml), and the resulting solution was added dropwise to a solution of benzyloxysodium (36.0 mmol) in tetrahydrofuran (50 ml) under cooling with ice. After stirring the mixture at room temperature for 30 minutes, a saturated aqueous solution of ammonium chloride was added thereto while cooling with ice, and the mixture was extracted with ethyl acetate. The extract was washed successively with water and a saturated aqueous solution of sodium chloride, and dried over anhydrous sodium sulfate. The solvent was removed by evaporation, and the residue was purified by silica gel column chromatography (n-hexane:ethyl acetate=1:1) to give the title compound (3.39 g, 7.02 mmol, 24%) as a colorless oily substance.

Reference Example 14
(1R,2R,6S)-1-(N-Benzyl-N-benzyloxycarbonyl)amino-4-p-anisoyl-4-azatricyclo[6.1.0.0$^{2,6}$]nonane A 1M n-hexane solution (20.0 ml) of diethylzinc (20.0 mmol) was added dropwise to a solution of (1R,5S)-2-(N-benzyl-N-benzyloxycarbonyl)amino-7-anisoyl-7-azabicyclo[3.3.0]oct-2-ene (3.39 g, 7.02 mmol) and diiodomethane (3.06 ml, 38.0 mmol) in dichloromethane (50 ml) at room temperature, followed by stirring for 16 hours. To the reaction mixture was added a saturated aqueous solution of ammonium chloride, and the mixture was extracted with ethyl acetate. The organic layer was washed with a sodium thiosulfate aqueous solution and a saturated sodium chloride aqueous solution, and dried over anhydrous sodium sulfate. The solvent was evaporated, and the residue was purified by silica gel column chromatography (n-hexane:ethyl acetate=1:1) to give 2.64 g (5.32 mmol, 76%) of the title compound as a colorless oily substance.

Reference Example 15
(1R,2R,6S)-1-t-Butoxycarbonylamino-4-p-anisoyl-4-azatricyclo[6.1.0.0$^{2,6}$]nonane To a methanol (100 ml) solution of (1R,2R,6S)-1-(N-benzyl-N-benzyloxycarbonyl)amino-4-p-anisoyl-4-azatricyclo[6.1.0.0$^{2,6}$]nonane (2.64 g, 5.32 mmol) was added 10% palladium-on-carbon (2.0 g), and the mixture was stirred vigorously in a hydrogen atmosphere for 15 hours. The insoluble matter was removed by Celite filtration, and the filtrate was concentrated. The residue and triethylamine (1.39 ml, 10.0 mmol) were dissolved in dichloromethane (50 ml), and di-t-butyl dicarbonate (2.18 g, 10 mmol) was added to the solution at room temperature, followed by stirring for 2 hours. After concentration, the residue was purified by silica gel column chromatography (n-hexane:ethyl acetate=1:2) to give 970 mg (2.60 mmol, 49%) of the title compound as a colorless oily substance.

Reference Example 16
(1R,2R,6S)-1-t-Butoxycarbonylamino-4-p-methoxybenzyl-4-azatricyclo[6.1.0.0$^{2,6}$]nonane A 1M tetrahydrofuran solution (7.0 ml) of a borane-tetrahydrofuran complex (7.0 mmol) was added dropwise to a tetrahydrofuran (20 ml) solution of (1R,2R,6S)-1-t-butoxycarbonylamino-4-p-anisoyl-4-azatricyclo[6.1.0.0$^{2,6}$]nonane (970 ml, 2.60 mmol) while cooling with ice, and the mixture was stirred at room temperature for 1 hour. While cooling with ice, water was added to the reaction mixture to decompose the excess borane-tetrahydrofuran complex. A 1N sodium hydroxide aqueous solution (10 ml) was added thereto, followed by refluxing for 6 hours. After cooling to room temperature, the reaction mixture was extracted with diethyl ether. The extract was dried over anhydrous sodium sulfate, the solvent was evaporated, and the residue was purified by silica gel column chromatography (chloroform:methanol=20:1) to give 453 mg (1.26 mmol, 48%) of the title compound as a colorless oily substance.

Reference Example 17
(1R,2R,6S)-1-t-butoxycarbonylamino-4-azatricyclo[6.1.0.0$^{2,6}$]nonane To a methanol (20 ml) solution of the (1R,2R,6S)-1-t-butoxycarbonylamino-4-p-methoxybenzyl-4-azatricyclo[6.1.0.0$^{2,6}$]-nonane (453 mg, 1.26 mmol) was added 10% palladium-on-carbon (400 mg), and the mixture was stirred vigorously in a pressurized (5 kg/cm$^2$) hydrogen atmosphere for 30 hours. The insoluble matter was removed by Celite filtration, and the filtrate was concentrated to give 286 mg (1.20 mmol, 95%) of the title compound as a colorless oily substance.

Reference Example 18
(1R,5S)-2-(N-Benzyl-N-benzyloxycarbonyl)amino-7-benzyloxycarbonyl-7-azabicyclo[3.3.0]oct-2-ene Benzylamine (546 µl, 5.0 mmol) was added dropwise to a mixture of (1R,5S)-7-benzyloxycarbonyl-2-oxo-7-azabicyclo[3.3.0]octane (1.0 g, 3.86 mmol), anhydrous magnesium sulfate (1.5 g), and tetrahydrofuran (15 ml) under cooling with ice, followed by stirring for 1 hour. The insoluble matter was removed by filtration, and the filtrate was concentrated. The residue was dissolved in benzene (15 ml), and triethylamine (753 µl, 35.0 mmol) was added thereto. To the mixture was further added triphosgene (534 mg, 1.8 mmol) under ice-cooling, and the mixture was stirred at room temperature for 1 hour. The insoluble matter was removed by Celite filtration, and the filtrate was concentrated. The residue was dissolved in tetrahydrofuran (10 ml), and the resulting solution was added dropwise to a solution of benzyloxysodium (6.0 mmol) in tetrahydrofuran (5 ml) under cooling with ice. After stirring the mixture at room temperature for 30 minutes, a saturated aqueous solution of ammonium chloride was added thereto while cooling with ice, and the mixture was extracted with ethyl acetate. The extract was washed successively with water and a saturated aqueous solution of sodium chloride, and dried over anhydrous sodium sulfate. The solvent was removed by evaporation, and the residue was dissolved indichloromethane (15 ml). Triethylamine (1.25 ml, 9.0 mmol) and 4-dimethylaminopyridine (50 mg) were added to the solution, and acetic anhydride (660 µl, 7.0 mmol) was added thereto dropwise at room temperature. After stirring at room temperature for 30 minutes, the reaction mixture was poured into a 10% aqueous solution of citric acid, followed by extraction with ethyl acetate. The organic layer was washed successively with a saturated sodium hydrogencarbonate aqueous solution and then a saturated sodium chloride aqueous solution, and dried over anhydrous sodium sulfate. The solvent was evaporated, and the residue was purified by silica gel column chromatography (n-hexane:ethyl acetate= 1:1) to give 1.07 g (2.22 mmol, 58%) of the title compound as a colorless oily substance.

Reference Example 19
(1R,2R,6S)-1-(N-Benzyl-N-benzyloxycarbonyl)amino-4-benzyloxycarbonyl-4-azatricyclo[6.1.0.0$^{2,6}$]nonane A 1M n-hexane solution (10.0 ml) of diethylzinc (10.0 mmol) was added dropwise to a solution of (1R,5S)-2-(N-benzyl-N-benzyloxycarbonyl)amino-7-benzyloxycarbonyl-7-azabicyclo[3.3.0]oct-2-ene (1.07 g, 2.22 mmol) and diiodomethane (1.57 ml, 19.5 mmol) indichloromethane (15 ml) at room temperature, followed by stirring for 16 hours. To the reaction mixture was added a saturated aqueous solution of ammonium chloride, and the mixture was extracted with ethyl acetate. The organic layer was washed successively with a sodium thiosulfate aqueous solution and a saturated sodium chloride aqueous solution, and dried over anhydrous sodium sulfate. The solvent was evaporated, and the residue was purified by silica gel column chromatography (n-hexane:ethyl acetate=3:1) to give 785 mg (1.58 mmol, 71%) of the title compound as a colorless oily substance.

Reference Example 20
(1R,2R,6S)-1-Amino-4-azatricyclo[6.1.0.0$^{2,6}$]nonane To a methanol (30 ml) solution of the (1R,2R,6S)-1-(N-benzyl-N-benzyloxycarbonyl)amino-4-benzyloxycarbonyl-4-azatricyclo[6.1.0.0$^{2,6}$]nonane (785 mg, 1.58 mmol) was added 10% palladium-on-carbon (800 mg), and the mixture was vigorously stirred in a hydrogen atmosphere for 9 hours. The insoluble matter was removed by Celite filtration, and the filtrate was concentrated to give 283 mg of the title compound as a colorless oily substance. [α]$_D$=−21.15 (c=0.26, methanol, T=24.5° C.)

Reference Example 21
Spiro[7'-benzyloxycarbonyl-7'-azabicyclo[3.3.0]octane-1,2'-2,5-dioxolane]

Ethylene glycol (44.6 ml, 800 mmol) and p-toluenesulfonic acid monohydrate (951 mg, 5 mmol) were added to a solution of 7-benzyloxycarbonyl-2-oxo-7-azabicyclo[3.3.0]octane (90.69 g, 350 mmol) in benzene (800 ml), and the mixture was refluxed for 3 hours while removing water produced with a Dean-Stark apparatus. After cooling to room temperature, the reaction mixture was poured into a saturated aqueous solution of sodium hydrogencarbonate and extracted with ethyl acetate. The organic layer was washed successively with water and a saturated sodium chloride aqueous solution and dried over anhydrous sodium sulfate. The solvent was evaporated to give 104.15 g (343 mmol, 98%) of the title compound as a crude colorless oily substance.

$^1$H-NMR (400 MHz, CDCl$_3$) δ: 1.45–1.53 (1H, m), 1.75–1.83 (1H, m), 1.89–2.01 (2H, m), 2.61 (1H, dt, J=5.5, 9.0 Hz), 2.74–2.84 (1H, m), 3.23–3.33 (1H, m), 3.44–3.62 (3H, m), 3.90–3.92 (4H, m), 5.11–5.14 (2H, m), 7.28–7.37 (5H, m).

Reference Example 22
Spiro[7'-azabicyclo[3.3.0]octane-1,2'-2,5-dioxolane]

To a methanol (1000 ml) solution of the crude spiro[7'-benzyloxycarbonyl-7'-azabicyclo[3.3.0]octane-1,2'-2,5-dioxolane] (104.15 g, 343 mmol) was added 10% palladium-on-carbon (15 g), and the mixture was vigorously stirred in a hydrogen atmosphere for 2 hours. The insoluble matter was removed by Celite filtration, and the filtrate was concentrated to give the title compound as a crude colorless oily substance in a quantitative yield. $^1$H-NMR (400 MHz, CDCl$_3$) δ: 1.26–1.34 (1H, m), 1.63–1.69 (1H, m), 1.73–1.80 (1H, m), 1.93 (1H, dq, J=7.5, 12.5 Hz), 2.48–2.53 (1H, m), 2.62–2.71 (2H, m), 2.76 (1H, dd, J=8.0, 12.0 Hz), 2.92 (1H, dd, J=7.0, 11.0 Hz), 3.00 (1H, dd, J=4.0, 12.0 Hz), 3.88–3.95 (4H, m)

Reference Example 23
Spiro[7'-azabicyclo[3.3.0]octane-1,2'-2,5-dioxolane] L(+)-Tartrate (F1)

A methanol (200 ml) solution of spiro[7'-azabicyclo[3.3.0]octane-1,2'-2,5-dioxolane] (39.46 g, 233 mmol) was added to a methanol (550 ml) solution of L(+)-tartaric acid (34.97 g, 233 mmol). The mixture was heated under reflux for 2 hours, followed by filtration to collect the precipitated crystals (37.70 g). The crystals were suspended in methanol (380 ml), followed by heating under reflux for 2 hours. The precipitated crystals (29.73 g) were collected by filtration, again suspended in methanol (300 ml), and heat-refluxed for 6 hours, followed by filtration to collect precipitated crystals (26.49 g). $^1$H-NMR (400 MHz, D$_2$O) δ: 1.43–1.51 (1H, m), 1.73–1.81 (1H, m), 1.89–2.05 (2H, m), 2.84–2.91 (1H, m), 2.95–3.07 (2H, m), 3.26–3.35 (2H, m), 3.42 (1H, dd, J=8.0, 11.5 Hz), 3.97 (4H, s), 4.47 (2H, s).

Reference Example 24
Spiro[7'-p-anisoyl-7'-azabicyclo[3.3.0]octane-1,2'-2,5-dioxolane] (F1)

The spiro[7'-azabicyclo[3.3.0]octane-1,2'-2,5-dioxolane] L(+)-tartrate (48.7 g, 153 mmol) was added to a mixture of a 2N sodium hydroxide aqueous solution (300 ml) and tetrahydrofuran (400 ml) under cooling with ice. A tetrahydrofuran (100 ml) solution of p-anisoyl chloride (34.12 g, 200 mmol) was added thereto dropwise, followed by stirring at room temperature for 1 hour. The organic layer was separated, washed successively with a 10% citric acid aqueous solution and a saturated sodium chloride aqueous solution, and dried over anhydrous sodium sulfate. The solvent was evaporated, and the residue was purified by silica gel column chromatography (n-hexane:ethyl acetate=1:1) to give 45.23 g (149 mmol, 97%) of the title compound as a colorless oily substance. The TLC and $^1$H-NMR data of the product were in agreement with those of Reference Example 11. HPLC analysis under the following conditions proved that the optical purity of the product was 98.4% ee.

HPLC Conditions

Column: DAICEL CHIRALCEL AD; 0.46×25 cm

Mobile Layer: hexane:ethanol=1:2

Flow Rate: 0.5 ml/min

Detection: UV (254 nm)

Reference Example 25
Spiro[7'-p-anisoyl-7'-azabicyclo[3.3.0]octane-1,2'-2,5-dioxolane]

p-Anisoyl chloride (17.1 g, 100 mmol) was added to a solution of spiro[7'-azabicyclo[3.3.0]octane-1,2'-2,5-dioxolane] (15.5 g, 91.8 mmol) and triethylamine (20.9 ml, 150 mmol) in dichloromethane (300 ml) under ice-cooling. The mixture was stirred at room temperature for 30 minutes, and the reaction mixture was poured into a 10% aqueous citric acid solution and extracted with ethyl acetate. The organic layer was washed successively with a saturated aqueous solution of sodium hydrogencarbonate and a saturated aqueous solution of sodium chloride and dried over anhydrous sodium sulfate. The solvent was evaporated, and the residue was purified by silica gel column chromatography (chloroform:methanol=50:1) to give 27.6 g (90.9 mmol, 99%) of the title compound as a colorless oily substance.

Reference Example 26
(+)-7-p-Anisoyl-2-oxo-7-azabicyclo[3.3.0]octane (F1)

Spiro[7'-anisoyl-7'-azabicyclo[3.3.0]octane-1,2'-2,5-dioxolane] (27.6 g, 90.9 mmol) was dissolved in 80% acetic acid (450 ml), and the solution was heat-refluxed for 2.5 hours. After cooling the reaction mixture to room temperature, the acetic acid was evaporated. To the residue was added a saturated aqueous solution of sodium hydrogencarbonate, and the mixture was extracted with ethyl acetate. The organic layer was washed with a saturated sodium chloride aqueous solution and dried over anhydrous sodium sulfate. The solvent was removed by evaporation, and the residue was purified by silica gel column chromatography (n-hexane:ethyl acetate=1:1) to give 24.1 g (quantitative) of a racemate of the title compound as a colorless oily substance. The TLC and $^1$H-NMR data of the product were in agreement with those of the product of Reference Example 12 (optically active compound). The resulting product was separated into the optically active compounds by HPLC under the following conditions to give 10.1 g (42%) of a high-polar optically active compound (F1) and 9.69 g (40%) of a low-polar optically active compound (F2).

HPLC Conditions
　Column: DAICEL CHIRALCEL AD; 2×25 cm
　Mobile Layer: hexane:ethanol:methanol=1:1:1
　Flow Rate: 5 ml/min
　Detection: UV (254 nm)
F1:
$[\alpha]_D$=77.1 (c=0.18, methanol, T=23.7° C.)
F2:
$[\alpha]_D$=−69.2 (c=0.29, methanol, T=23.7° C.)

Each of the resulting optically active compounds (F1 and F2) was led to 1-t-butoxycarbonylamino-4-azatricyclo[6.1.0.0$^{2,6}$]nonane (F1 and F2) in accordance with Reference Examples 13, 14, 15, 16, and 17.

EXAMPLE 2

10-{(1R,2R,6S)-1-Amino-4-azatricyclo[6.1.0.0$^{2,6}$]nonan-4-yl}-9-fluoro-2,3-dihydro-3-(S)-methyl-7-oxo-7H-pyrido[1.2.3-de][1,4]benzoxazine-6-carboxylic Acid 9,10-Difluoro-2,3-dihydro-3-(S)-methyl-7-oxo-7H-pyrido[1.2.3-de][1,4]benzoxazine-6-carboxylic acid.BF$_2$ chelate (329 mg, 1.0 mmol) was added to a solution of (1R,2R,6S)-1-t-butoxycarbonylamino-4-azatricyclo[6.1.0.0$^{2,6}$]nonane (F1; 286 mg, 1.20 mmol) and triethylamine (348 μl, 2.5 mmol) in dimethyl sulfoxide (3 ml) at room temperature, followed by stirring at room temperature for 15 hours. Triethylamine was evaporated from the mixture, and water was added to the residue. The crystals thus precipitated were collected by filtration. To the crystals were added 90% methanol (30 ml) and triethylamine (5 ml), and the mixture was heated under reflux for 5 hours. Methanol was evaporated, and a 10% citric acid aqueous solution was added to the residue, and the mixture was extracted with chloroform. The organic layer was washed with a saturated aqueous solution of sodium chloride and dried over anhydrous sodium sulfate. The solvent was removed by evaporation, and the residue was dissolved in dichloromethane (5 ml). Trifluoroacetic acid (10 ml) was added to the solution while cooling with ice, and the mixture was stirred at room temperature for 1 hour, followed by concentration. To the residue was added a hydrochloric acid aqueous solution. The mixture was washed with chloroform, adjusted to pH 7.8 with a sodium hydroxide aqueous solution, and extracted with chloroform. The extract was dried over anhydrous sodium sulfate, and the solvent was evaporated. The residue was recrystallized from 2-propanol to give 124 mg (0.31 mmol, 31%) of the title compound as yellow crystals. $^1$H-NMR (400 MHz, 0.1N-NaOD) δ: 0.46–0.54 (1H, m), 0.55 (1H, dd, J=5.0, 8.5 Hz), 1.23 (1H, dt, J=4.0, 8.5 Hz), 1.41 (3H, d, J=7.0 Hz), 1.71–1.83 (2H, m), 2.22–2.32 (1H, m), 2.66 (1H, q, J=8.5 Hz), 3.13–3.17 (1H, m), 3.46 (1H, t, J=9.0 Hz), 3.70–3.81 (2H, m), 4.19–4.25 (1H, m), 4.38–4.41 (1H, m), 4.47–4.54 (1H, m), 7.43 (1H, d, J=13.5 Hz), 8.22 (1H, s)

$[\alpha]_D$=−93.00 (c=0.30, 1N NaOH aqueous solution, T=24.0° C.)

Melting point: 216–221° C. (decomposition)

Elemental Analysis for C$_{21}$H$_{22}$FN$_3$O$_4$: Calcd.: C, 63.15; H, 5.55; N, 10.52 Found: C, 62.90; H, 5.63; N, 10.22

EXAMPLE 3

10-{(1R,2R,6S)-1-Amino-4-azatricyclo[6.1.0.0$^{2,6}$]nonan-4-yl}-9-fluoro-2,3-dihydro-3-(S)-methyl-7-oxo-7H-pyrido[1.2.3-de][1,4]benzoxazine-6-carboxylic Acid 9,10-Difluoro-2,3-dihydro-3-(S)-methyl-7-oxo-7H-pyrido[1.2.3-de][1,4]benzoxazine-6-carboxylic acid.BF$_2$ chelate (74 mg, 0.225 mmol) was added to a solution of (1R,2R,6S)-1-amino-4-azatricyclo[6.1.0.0$^{2,6}$]nonane (73.6 mg, 0.533 mmol) and triethylamine (74.3 μl, 0.533 mmol) in dimethyl sulfoxide (3 ml) at room temperature, followed by stirring at room temperature for 5 hours. The solvent was evaporated, and to the residue were added 90% ethanol (40 ml) and triethylamine (1 ml). The mixture was heated under reflux for 3 hours. The ethanol was evaporated, and a hydrochloric acid aqueous solution was added to the residue. The mixture was washed with chloroform, adjusted to pH 7.4 with a sodium hydroxide aqueous solution, and extracted with chloroform. The extract was dried over anhydrous sodium sulfate. The solvent was removed by evaporation, and the residue was recrystallized from ethanol to give 69 mg (0.173 mmol, 77%) of the title compound as yellow crystals. The $^1$H-NMR and specific rotation data of the product were in agreement with those of Example 1.

Elemental Analysis for C$_{21}$H$_{22}$FN$_3$O$_4$: Calcd.: C, 63.15; H, 5.55; N, 10.52 Found: C, 62.98; H, 5.77; N, 10.43

EXAMPLE 4

10-{1-Amino-4-azatricyclo[6.1.0.0$^{2,6}$]nonan-4-yl}-9-fluoro-2,3-dihydro-3-(S)-methyl-7oxo-7H-pyrido[1.2.3-de][1,4]benzoxazine-6-carboxylic Acid (F2)

9,10-Difluoro-2,3-dihydro-3-(S)-methyl-7-oxo-7H-pyrido[1.2.3-de][1,4]benzoxazine-6-carboxylic acid.BF$_2$ chelate (526 mg, 1.6 mmol) was added to a solution of (1S,2S,6R)-1-t-butoxycarbonylamino-4-azatricyclo[6.1.0.0$^{2,6}$]nonane (F2; 395 mg, 1.66 mmol) and triethylamine (557 μl, 4.0 mmol) in dimethyl sulfoxide (3 ml) at room temperature, followed by stirring at room temperature for 15 hours. Triethylamine was evaporated from the mixture, and water was added to the residue. The crystals thus precipitated were collected by filtration. To the crystals were added 90% methanol (30 ml) andtriethylamine (5 ml), and the mixture was heated under reflux for 5 hours. Methanol was evaporated, and a 10% citric acid aqueous solution was added to the residue, and the mixture was extracted with chloroform. The organic layer was washed with a saturated aqueous solution of sodium chloride and dried over anhydrous sodium sulfate. The solvent was removed by evaporation, and the residue was dissolved in dichloromethane (5 ml). Trifluoroacetic acid (10 ml) was added to the solution while cooling with ice, and the mixture was stirred at room temperature for 1 hour, followed by concentration. To the residue was added a hydrochloric acid aqueous solution, washed with chloroform, adjusted to pH 7.8 with a sodium hydroxide aqueous solution, and extracted with chloroform. The extract was dried over anhydrous sodium sulfate, and the solvent was evaporated. The residue was recrystallized from 2-propanol to give 180 mg (0.45 mmol, 28%) of the title compound as yellow crystals.

$^1$H-NMR (400MHz, 0.1N-NaOD) δ: 0.46–0.54 (1H, m), 0.55 (1H, dd, J=5.0, 8.5 Hz), 1.23 (1H, dt, J=4.0, 8.5 Hz), 1.39 (3H, d, J=7.0 Hz), 1.71–1.83 (2H, m), 2.22–2.32 (1H, m), 2.66 (1Hz q, J=8.5 Hz), 3.13–3.17 (1H, m), 3.46 (1H, t, J=9.0 Hz), 3.70–3.81 (2H, m), 4.19–4.25 (1H, m), 4.38–4.41 (1H, m), 4.47–4.54 (1H, m), 7.41 (1H, d, J=14.0 Hz), 8.20 (1H, s)

$[\alpha]_D$=−6.41 (c=0.39, 1N NaOH aqueous solution, T=24.2° C.)

Melting point: 176–180 (decomposition)

Elemental analysis for C$_{21}$H$_{22}$FN$_3$O$_4$: Calcd.: C, 63.15; H, 5.55; N, 10.52 Found: C, 63.01; H, 5.65; N, 10.29

EXAMPLE 5

7-{1-Amino-4-azatricyclo[6.1.0.0$^{2,6}$]nonan-4-yl}-6-fluoro-1-[2-(S)-fluoro-1-(R)-cyclopropyl]-1,4-dihydro-8-methoxy-4-oxoquinoline-3-carboxylic Acid (F1)

6,7-Difluoro-1-[2-(S)-fluoro-1-(R)-cyclopropyl]-1,4-dihydro-8-methoxy-4-oxoquinoline-3-carboxylic acid.BF$_2$ chelate (433 mg, 1.2 mmol) was added to a solution of 1-t-butoxycarbonylamino-4-azatricyclo[6.1.0.0$^{2,6}$]nonane (F1; 300 mg, 1.26 mmol) and triethylamine (697 μl, 5.0 mmol) in dimethyl sulfoxide (3 ml) at room temperature, followed by stirring at room temperature for 15 hours. Triethylamine was evaporated from the mixture, and water was added to the residue. The crystals thus precipitated were collected by filtration. To the crystals were added 90%methanol (30 ml) and triethylamine (5 ml), and the mixture was heated under reflux for 5 hours. Methanol was evaporated, and a 10% citric acid aqueous solution was added to the residue, and the mixture was extracted with chloroform. The organic layer was washed with a saturated aqueous solution of sodium chloride and dried over anhydrous sodium sulfate. The solvent was removed by evaporation, and the residue was dissolved in dichloromethane (5 ml). Trifluoroacetic acid (10 ml) was added to the solution while cooling with ice, and the mixture was stirred at room temperature for 1 hour, followed by concentration. To the residue was added a hydrochloric acid aqueous solution, washed with chloroform, adjusted to pH 7.8 with a sodium hydroxide aqueous solution, and extracted with chloroform. The extract was dried over anhydrous sodium sulfate, and the solvent was evaporated. The residue was recrystallized from 2-propanol to give 180 mg (0.41 mmol, 34%) of the title compound as yellow crystals.
$^1$H-NMR (400 MHz, 0.1N-NaOD) δ: 0.56–0.60 (2H, m), 1.25–1.35 (3H, m), 1.41–1.52 (1H, m), 1.72 (1H, ddd, J=4.0, 9.0, 13.0 Hz), 1.81 (1H, dd, J=8.5, 12.5 Hz), 2.26–2.34 (1H, m), 2.70 (1H, q, J=8.0 Hz), 3.23 (1H, d, J=10.5 Hz), 3.45 (1H, t, J=9.5 Hz), 3.53 (3H, s), 3.79–3.84 (2H, m), 3.95 (1H, dt, J=5.5, 9.0 Hz), 4.96 (1H, ddd, J=5.5, 8.5, 63.5 Hz), 7.59 (1H, d, J=14.5 Hz), 8.32 (1H, d, J=3.5 Hz)

[α]$_D$=−69.39 (c=0.49, NaOH aqueous solution, T=24.4° C.)

Melting point: 146–159° C. (decomposition)

Elemental analysis for $C_{22}H_{23}F_2N_3O_4 \cdot 0.5H_2O$: Calcd.: C, 59.99; H, 5.49; N, 9.54 Found: C, 59.79; H, 5.27; N, 9.49

EXAMPLE 6

5-Amino-7-{1-amino-4-azatricyclo[6.1.0.0$^{2,6}$]nonan-4-yl}-6-fluoro-1-[2-(S)-fluoro-1-(R)-cyclopropyl]-1,4-dihydro-8-methyl-4-oxoquinoline-4-carboxylic Acid (F1)

1-t-Butoxycarbonylamino-4-azatricyclo[6.1.0.0$^{2,6}$]nonane (F1; 498 mg, 2.09 mmol) and triethylamine (5 ml) were added to dimethyl sulfoxide (10 ml) at room temperature, and 5-amino-6,7-difluoro-1-[2-(S)-fluoro-1-(R)-cyclopropyl]-1,4-dihydro-8-methyl-4-oxoquinoline-3-carboxylic acid (625 mg, 2.0 mmol) was added thereto, followed by stirring at an external temperature of 120° C. for 15 hours. Triethylamine and dimethyl sulfoxide were removed by evaporation, and a 10% citric acid aqueous solution was added to the residue. The mixture was extracted with chloroform, and the extract was dried over anhydrous sodium sulfate. The solvent was evaporated, and concentrated hydrochloric acid was added to the residue. The mixture was washed with chloroform, adjusted to pH 7.8 with a sodium hydroxide aqueous solution, and extracted with chloroform. The extract was dried over anhydrous sodium sulfate, and the solvent was evaporated. The residue was recrystallized from 2-propanol to give 74 mg (0.17 mmol, 9%) of the title compound as yellow crystals.

$^1$H-NMR (400 MHz, 0.1N-NaOD) δ: 0.47 (1H, d, J=4.5 Hz), 0.56 (1H, dd, J=4.5, 8.0 Hz), 0.92–1.03 (1H, m), 1.24–1.26 (1H, m), 1.36–1.46 (1H, m), 1.62–1.67 (1H, m), 1.74 (1H, dd, J=8.0, 12.0 Hz), 2.17–2.26 (1H, m), 2.61 (1H, q, J=7.5 Hz), 2.87 (1H, d, J=9.5 Hz), 3.11 (1H, t, J=9.0 Hz), 3.69–4.03 (3H, m), 4.60–4.99 (1H, m), 8.20 (1H, d, J=3.5 Hz)

Elemental analysis for $C_{22}H_{24}F_2N_4O_3$: Calcd.: C, 61.39; H, 5.62; N, 13.02 Found: C, 61.59; H, 5.64; N, 12.77

Reference Example 27

(1R,5S)-2-(N-Benzyl-N-benzyloxycarbonyl)amino-7-p-anisoyl-7-azabicyclo[3.3.0]-oct-2-ene (alternative to the method of Reference Example 13)

A solution of benzylamine (10.9 ml, 100 mmol) in tetrahydrofuran (50 ml) was added dropwise to a mixture of (1R,5S)-7-p-anisoyl-2-oxo-7-azabicyclo[3.3.0]octane (20.72 g, 79.9 mmol), anhydrous magnesium sulfate (20 g), and tetrahydrofuran (200 ml) while cooling with ice. After stirring the mixture for 1 hour, the insoluble matter was removed by filtration, and the filtrate was concentrated. The residue thus obtained was dissolved in dichloromethane (100 ml), and N,N-dimethylaniline (15.2 ml, 120 mmol) was added to the solution. Benzyl chloroformate (17.13 ml, 120 mmol) was added dropwise to the mixture under ice-cooling, followed by stirring at room temperature for 2 hours. The reaction mixture was added to a 1N hydrochloric acid aqueous solution and extracted with ethyl acetate. The extract was washed successively with a saturated sodium hydrogencarbonate aqueous solution and a saturated sodium chloride aqueous solution and dried over anhydrous sodium sulfate. The solvent was removed by evaporation, and the residue was purified by silica gel column chromatography (n-hexane:ethyl acetate=1:1) to give 31.64 g (65.5 mmol, 82%) of the title compound as a colorless oily substance.

Reference Example 28

(1R,2R,6S)-1-t-Butoxycarbonylamino-4-p-methoxybenzyl-4-azatricyclo[6.1.0.0$^{2,6}$]nonane (alternative to the method of Reference Example 16)

Lithium aluminum hydride (1.37 g, 36 mmol) was added to a tetrahydrofuran (200 ml) solution of (1R,2R,6S)-1-t-butoxycarbonylamino-4-p-anisoyl-4-azatricyclo[6.1.0.0$^{2,6}$]nonane (13.40 g, 35.98 mmol) while cooling with ice, and the mixture was stirred at room temperature for 1 hour. To the reaction mixture were added dropwise water (1.37 ml), a 15% sodium hydroxide aqueous solution (1.37 ml), and water (4.11 ml) in this order while cooling with ice, followed by stirring at room temperature for 18 hours. The insoluble matter was removed by Celite filtration, and the filtrate was concentrated. The residue was purified by silica gel column chromatography (chloroform:methanol=20:1) to give 8.24 g (23.00 mmol, 64%) of the title compound as a colorless oily substance.

Reference Example 29

(1R,5S)-2-(N-Benzyl-N-benzyloxycarbonyl)amino-7-benzyloxycarbonyl-7-azabicyclo[3.3.0]oct-2-ene Lithium aluminum hydride (1.37 g, 36 mmol) was added to a tetrahydrofuran (200 ml) solution of (1R,5S)-1-t-butoxycarbonylamino-4-p-anisoyl-4-azatricyclo[6.1.0.0$^{2,6}$]nonane (13.40 g, 35.98 mmol) while cooling with ice, and the mixture was stirred at room temperature for 1 hour. To the reaction mixture were added dropwise water (1.37 ml), a 15% sodium hydroxide aqueous solution (1.37 ml), and water (4.11 ml) in this order while cooling with ice, followed by stirring at room temperature for 18 hours. The insoluble matter was removed by Celite filtration, and the filtrate was concentrated. The residue was purified by silica gel column chromatography (chloroform:methanol=20:1) to give 8.24 g (23.00 mmol, 64%) of the title compound as a colorless oily substance.

Reference Example 30
11-Aza-11-benzyl-tetracyclo[7.3.1$^{4,7}$0$^{3,8}$0]tridec-5-en-2-one Benzylbutoxymethyltrimethylsilylamine (4.59 g, 16.4 mmol) was added to a dichloroethane (15 ml) solution of tricyclo[5.2.1.0$^{2,6}$]deca-4,8-dien-3-one (Synthesis, p. 687 (1994)) (2.00 g, 13.7 mmol), and trifluoroacetic acid (15 µl) was further added thereto at room temperature. The mixture was stirred at that temperature for 2 hours and then at 50° C. for 16 hours. A 10% citric acid aqueous solution was added to the reaction mixture. The organic layer was separated, and to the aqueous layer was added a saturated sodium hydrogencarbonate aqueous solution, followed by extraction with dichloromethane. The organic layer was dried over anhydrous sodium sulfate. The solvent was removed by evaporation to give 3.40 g (89%) of the title compound as a crude product. The product was used in the subsequent reaction without purification. $^1$H-NMR (CDCl$_3$) δ: 1.38 (1H, d, J=8.3 Hz), 2.18–2.22 (1H, m), 2.32–2.37 (3H, m), 2.44–2.48 (1H, m), 2.63–2.68 (2H, m), 2.88 (1H, d, J=7.8 Hz), 3.00–3.06 (2H, m), 3.20–3.22 (1H, m), 3.47 (2H, AB-q, J=13.2 Hz), 6.06–6.08 (1H, m), 6.15–6.17 (1H, m), 7.22–7.31 (5H, m)

Reference Example 31
7-Benzyl-2-oxo-7-azabicyclo[3.3.0]oct-3-ene

A solution of 11-aza-11-benzyl-tetracyclo[7.3.1$^{4,7}$0$^{3,8}$0]tridec-5-en-2-one (3.40 g, 12.17 mmol) in diphenyl ether (70 ml) was stirred at 220° C. for 20 minutes. To the reaction mixture was further added diphenyl ether (130 ml), followed by stirring at 220° C. for an additional 20 minute period. After cooling to room temperature, diethyl ether was added thereto, and the reaction mixture was extracted with a 10% citric acid aqueous solution. The combined aqueous layer was washed with dichloromethane. Sodium hydrogencarbonate was added thereto, and a saturated sodium hydrogencarbonate aqueous solution was added to make the mixture alkaline. The mixture was extracted with dichloromethane. The organic layer was dried over anhydrous sodium sulfate. The solvent was evaporated, and the residue was purified by silica gel column chromatography (n-hexane:ethyl acetate=1:1) to give 1.45 g (56%) of the title compound.
$^1$H-NMR (CDCl$_3$) δ: 2.31 (1H, t, J=8.8 Hz), 2.36 (1H, t, J=8.8 Hz), 2.71–2.75 (1H, m), 2.79 (1H, d, J=9.3 Hz), 3.10 (1H, d, J=9.3 Hz), 3.36–3.41 (1H, m), 3.55 (2H, AB-q, J=13.2 Hz), 6.24 (1H, d, J=5.4 Hz), 7.20–7.35 (5H, m), 7.55 (1H, dd, J=3.0, 5.8 Hz)

Reference Example 32
7-Benzyl-2-oxo-7-azabicyclo[3.3.0]octane

To an ethyl acetate (50 ml) solution of 7-benzyl-2-oxo-7-azabicyclo[3.3.0]oct-3-ene (1.45 g, 6.78 mmol) was added 5% rhodium-on-alumina (700 mg), and the mixture was stirred vigorously in a hydrogen atmosphere for 3.5 hours. The insoluble matter was removed by Celite filtration, and the filtrate was concentrated. The residue was purified by silica gel column chromatography (n-hexane:ethyl acetate=1:1) to give 1.22 g (5.70 mmol, 84%) of the title compound as a colorless oily substance. The TLC and $^1$H-NMR data of the product were in agreement with those of the product of Reference Example 1.

EXAMPLE 7
7-(1-Amino-4-azabicyclo[6.1.0.0$^{2,6}$]nonan-4-yl)-6-fluoro-1-[2-(S)-fluoro-1-(R)-cyclopropyl]-8-methyl-1,4-dihydro-4-oxoquinoline-3-carboxylic Acid (1R,2R,6S)-1-t-Butoxycarbonylamino-4-azatricyclo-[6.1.0.0$^{2,6}$]nonane (1.20 mmol) was dissolved in dimethyl sulfoxide (1.2 ml), and 6,7-difluoro-1-[2-(S)-fluoro-1-(R)-cyclopropyl]-1,4-dihydro-8-methyl-4-oxoquinoline-3-carboxylic acid.BF$_2$ chelate (345 mg, 1.00 mmol) and triethylamine (0.167 ml) were added to the solution. The mixture was stirred in a nitrogen atmosphere for 132 hours. The solvent was removed by evaporation, and water was added to the residue. Yellow crystals thus precipitated were collected by filtration and washed with water. To the crystals were added 90% methanol (50 ml) and triethylamine (2 ml), and the mixture was heated under reflux for 3 hours. Methanol was evaporated, and concentrated hydrochloric acid (10 ml) was added dropwise to the residue while cooling with ice, followed by stirring at room temperature for 1 hour. Water (20 ml) was added to the reaction mixture, and the mixture was washed with chloroform (30 ml×3), adjusted to pH 12.0 with a sodium hydroxide aqueous solution, then adjusted to pH 7.4 with 1N hydrochloric acid, and extracted with chloroform (150 ml×3). The combined organic layer was dried over anhydrous sodium sulfate. After filtration, the filtrate was concentrated under reduced pressure. The residue was purified by preparative TLC. The resulting crude product was recrystallized from ethanol and dried under reduced pressure to give 51 mg (12%) of the title compound as yellow powder.
$^1$H-NMR (400 MHz, 0.1NaOD) δ: 0.59–0.67 (2H, m), 1.37–1.40 (1H, m), 1.57–1.65 (1H, m), 1.80–1.89 (2H, m), 2.37–2.41 (1H, m), 2.53 (3H, s), 2.77–2.85 (1H, m), 3.04–3.09 (1H, m), 3.27–3.36 (1H, m), 3.83–3.93 (1H, m), 4.05–4.11 (1H, m), 5.04 (1H, brd, J=58.19 Hz), 7.71 (1H, d, J=14.16 Hz), 8.44 (1H, d, J=3.41 Hz)

Elemental analysis for C$_{22}$H$_{23}$F$_2$N$_3$O$_3$.0.5H$_2$O: Calcd.: C, 62.25; H, 5.70; N, 9.90 Found: C, 62.05; H, 5.54; N, 9.61

The antimicrobial activity of the compounds according to the present invention was determined in accordance with the standard method specified by the Japan Chemotherapeutic Society. The results obtained, being expressed in terms of minimum inhibitory concentration (MIC; µg/ml), are shown in the following Table.

| | Compound of Example | | | | |
|---|---|---|---|---|---|
| Microorganism | 1 | 2 | 5 | 6 | 7 |
| E. coil, NIHJ | ≦0.003 | ≦0.003 | ≦0.003 | ≦0.003 | ≦0.003 |
| S. flexneli, 2A 5503 | ≦0.003 | 0.006 | ≦0.003 | ≦0.003 | ≦0.003 |
| Pr. vulgaris, 08601 | 0.10 | 0.025 | 0.006 | 0.025 | ≦0.003 |
| Pr. Mirabilis, IFO-3849 | 0.05 | 0.10 | ≦0.003 | 0.025 | 0.013 |
| Ser. Marcescens, 10100 | 0.10 | 0.05 | 0.05 | 0.05 | 0.025 |
| Ps. Aeruginosa, 32104 | 0.20 | 0.20 | 0.10 | 0.10 | 0.05 |
| Ps. Aeruginosa, 32121 | 0.20 | 0.05 | 0.05 | 0.025 | 0.025 |
| Ps. Maltophilia, 11D-1275 | 0.05 | 0.20 | 0.05 | 0.025 | 0.025 |
| S. aureaus, 209P | ≦0.003 | 0.006 | ≦0.003 | ≦0.003 | ≦0.003 |
| S. epidermidis, 56500 | 0.006 | 0.025 | ≦0.003 | ≦0.003 | ≦0.003 |
| Str. Pyogenes, G-36 | 0.006 | 0.013 | ≦0.003 | ≦0.003 | ≦0.003 |
| Str. Faecalis, ATCC-19433 | 0.025 | 0.05 | 0.025 | 0.013 | 0.013 |
| S. aureus, 870307 | 0.10 | 0.20 | 0.013 | 0.05 | 0.013 |
| S. pneumoniae, J24 | ≦0.003 | 0.013 | ≦0.003 | ≦0.003 | ≦0.003 |

Industrial Applicability

The compound according to the present invention possesses excellent antimicrobial activity over a broad range of both Gram negative and Gram positive bacteria and, in particular, exhibits potent antimicrobial activity even on quinolone-resistant bacteria, while showing satisfactory pharmacokinatics and safety, and are useful as an antimicrobial compound.

What is claimed is:

1. A compound which is 1-(N-Benzyl-N-benzyloxycarbonyl)amino-4-benzyloxycarbonyl-4-azatricyclo[6.1.0.0$^{2,6}$]nonane or a salt or hydrate thereof, or a hydrate of the salt.

2. A compound which is 1-Amino-4-azatricyclo[6.1.0.0$^{2,6}$]nonane or a salt or hydrate thereof, or a hydrate of the salt.

3. A compound which is (1R,2R,6S)-1-(N-Benzyl-N-benzyloxycarbonyl)amino-4-p-anisoyl-4-azatricyclo[6.1.0.0$^{2,6}$]nonane or a salt or hydrate thereof, or a hydrate of the salt.

4. A compound which is (1R,2R,6S)-1-t-Butoxycarbonylamino-4-p-anisoyl-4-azatricyclo[6.1.0.0$^{2,6}$]nonane or a salt or hydrate thereof, or a hydrate of the salt.

5. A compound which is (1R,2R,6S)-1-t-Butoxycarbonylamino-4-p-methoxybenzyl-4-azatricyclo[6.1.0.0$^{2,6}$]nonane or a salt or hydrate thereof, or a hydrate of the salt.

6. A compound which is (1R,2R,6S)-1-t-Butoxycarbonylamino-4-azatricyclo[6.1.0.0$^{2,6}$]nonane or a salt or hydrate thereof, or a hydrate of the salt.

7. A compound which is (1R,2R,6S)-1-(N-Benzyl-N-benzyloxycarbonyl)amino-4-benzyloxycarbonyl-4 azatricyclo[6.1.0.0$^{2,6}$]nonane or a salt or hydrate thereof, or a hydrate of the salt.

8. A compound which is (1R,2R,6S)-1-Amino-4-azatricyclo[6.1.0.0$^{2,6}$]nonane, or a salt or hydrate thereof, or a hydrate of the salt.

* * * * *